US006201989B1

(12) United States Patent
Whitehead et al.

(10) Patent No.: US 6,201,989 B1
(45) Date of Patent: Mar. 13, 2001

(54) METHODS AND APPARATUS FOR DETECTING THE REJECTION OF TRANSPLANTED TISSUE

(75) Inventors: Peter D. Whitehead, West Vancouver; Calum E. MacAulay; Nicholas B. MacKinnon, both of Vancouver; Haishan Zeng, Delta; Christopher R. Thompson, West Vancouver; Bruce M. McManus, Vancouver, all of (CA)

(73) Assignee: Biomax Technologies Inc., Vancouver (CA)

( * ) Notice: Subject to any disclaimer, the term of this patent is extended or adjusted under 35 U.S.C. 154(b) by 0 days.

(21) Appl. No.: 09/041,861

(22) Filed: Mar. 12, 1998

Related U.S. Application Data

(60) Provisional application No. 60/040,557, filed on Mar. 13, 1997, provisional application No. 60/046,368, filed on May 15, 1997, provisional application No. 60/062,512, filed on Oct. 16, 1997, and provisional application No. 60/068,693, filed on Dec. 23, 1997.

(51) Int. Cl.[7] .................................................. A61B 6/00
(52) U.S. Cl. ........................ 600/476; 250/461.2; 600/477
(58) Field of Search ................................. 600/473, 476, 600/477, 478, 310; 356/432; 250/458.1, 461.1, 461.2, 483.1, 484.2, 484.4, 492.1, 358.1

(56) References Cited

U.S. PATENT DOCUMENTS

| 3,924,608 | 12/1975 | Mitsui | 128/2 B |
| 3,961,621 | 6/1976 | Northeved | 128/2 B |
| 4,421,106 | 12/1983 | Uehara | 128/4 |
| 4,557,255 | 12/1985 | Goodman | 128/7 |
| 4,573,450 | 3/1986 | Arakawa | 128/6 |
| 4,620,547 | 11/1986 | Boebel | 128/754 |

(List continued on next page.)

FOREIGN PATENT DOCUMENTS

| 39 20 706 A1 | 1/1991 | (DE) | A61B/10/00 |
| 321 132 A2 | 6/1989 | (EP) | A61M/25/00 |
| 783 867 A1 | 7/1997 | (EP) | A61B/5/103 |
| WO 83/03189 | 9/1983 | (WO) | A61B/1/06 |
| WO 94/12095 | 6/1994 | (WO) | A61B/5/00 |
| WO 94/16622 | 8/1994 | (WO) | A61B/6/00 |
| WO 94/26168 | 11/1994 | (WO) . | |
| WO 96/39925 | 12/1996 | (WO) | A61B/5/00 |
| WO 97/41776 | 11/1997 | (WO) | A61B/10/00 |
| WO 97/41777 | 11/1997 | (WO) | A61B/10/00 |

OTHER PUBLICATIONS

Barry et al., Fourier Transform Raman and Infrared Vibrational Study of Human Skin: Assignment of Spectral Bands. *Journal of Raman Spectroscopy*, 23:641–645, 1992.

Bohorfoush, Tissue Spectroscopy for Gastrointestinal Diseases. *Endoscopy*, 28:372–380, 1996.

Feld et al., Detection and characterization of human tissue lesions with near infrared Raman spectroscopy. SPIE Proceedings, 2388:99–104, 1995.

(List continued on next page.)

*Primary Examiner*—Brian L. Casler
(74) *Attorney, Agent, or Firm*—Graybeal Jackson Haley LLP

(57) ABSTRACT

Methods and apparatus for detecting the possible rejection of a transplanted tissue by a host. The transplanted tissue is subjected to illumination with light to induce fluorescence. The light can be ultraviolet light, visible light or infrared light, which can be used alone or in any combination, which means one, two or three forms of light may be used together. The induced fluorescence is collected and analyzed, then compared with fluorescence that is obtained using the same procedure for a known, healthy tissue that is the same type of tissue as the transplanted tissue. Also provided are methods and apparatus related to the determination of probe orientation and the need for biopsy.

20 Claims, 20 Drawing Sheets

U.S. PATENT DOCUMENTS

| | | | |
|---|---|---|---|
| 4,656,999 | 4/1987 | Storz | 128/4 |
| 4,718,417 | 1/1988 | Kittrell et al. | 128/303.1 |
| 4,887,612 | 12/1989 | Esser et al. | 128/751 |
| 4,927,222 | 5/1990 | Kamiya et al. | 350/96.15 |
| 4,930,516 | 6/1990 | Alfano et al. | 128/665 |
| 4,957,144 | 9/1990 | Zeng et al. | 128/665 |
| 5,042,494 | 8/1991 | Alfano | 128/665 |
| 5,115,137 | 5/1992 | Andersson-Engels et al. | 250/461.2 |
| 5,131,398 | 7/1992 | Alfano | 128/665 |
| 5,261,410 | 11/1993 | Alfano et al. | 128/664 |
| 5,280,788 | 1/1994 | Janes et al. | 128/665 |
| 5,287,857 | 2/1994 | Mann | 128/753 |
| 5,291,010 | 3/1994 | Tsuji | 250/208.1 |
| 5,293,872 | 3/1994 | Alfano et al. | 128/665 |
| 5,304,173 | 4/1994 | Kittrell et al. | 606/15 |
| 5,318,023 | 6/1994 | Vari et al. | 128/633 |
| 5,345,941 | 9/1994 | Rava et al. | 128/665 |
| 5,348,018 | 9/1994 | Alfano et al. | 128/665 |
| 5,406,959 | 4/1995 | Mann | 128/753 |
| 5,413,108 | 5/1995 | Alfano | 128/665 |
| 5,439,000 | 8/1995 | Gunderson et al. | 128/664 |
| 5,450,857 | 9/1995 | Garfield et al. | 128/778 |
| 5,452,723 | 9/1995 | Wu et al. | 128/664 |
| 5,460,182 | 10/1995 | Goodman et al. | 128/664 |
| 5,467,767 | 11/1995 | Alfano et al. | 128/665 |
| 5,507,287 | 4/1996 | Palcic et al. | 128/633 |
| 5,579,773 | 12/1996 | Vo-Dinh et al. | 128/665 |
| 5,590,660 | 1/1997 | MacAulay et al. | 128/664 |
| 5,612,540 | 3/1997 | Richards-Kortum et al. | 250/461.5 |
| 5,647,368 | 7/1997 | Zeng et al. | 128/665 |
| 5,697,373 | 12/1997 | Richards-Kortum et al. | 128/664 |
| 5,699,795 | 12/1997 | Richards-Kortum et al. | 128/634 |
| 5,701,902 | 12/1997 | Vari et al. | 128/664 |
| 5,762,613 | 6/1998 | Sutton et al. | 600/564 |
| 5,908,445 | 6/1999 | Whayne et al. | 607/122 |
| 6,055,451 | 4/2000 | Bambot et al. | 600/476 |

OTHER PUBLICATIONS

Fercher, Optical Coherence Tomography. *Journal of Biomedical Optics,* 1(2):157–173, 1996.

Liu et al., Raman, fluorecence, and time–resolved light scattering as optical diagnostic techniques to separate diseased and normal biomedical media. *Journal of Photochemistry and Photobiology B: Biology,* 16:187–209, 1992.

Lui et al., Optical Spectroscopy as a Potential Diagnostic Aid for Dermatology. *Clinical Dermatology 2000—An International Congress,* Vancouver, BC, May 28–31, 1996, Programme and Abstracts Abstract 584, p. 176.

Lui et al., Ratio Analysis of Reflectance and Fluorescence Spectra of Diseased Skin. 24*th* Annual Meeting of the American Society for Photobiology, Atlanta, Georgia, Jun. 15–20, 1996.

Mahadevan–Jansen and Richards–Kortum, Raman Spectroscopy For The Detection Of Cancers And Precancers. *Journal of Biomedical Optics,* 1(1):31–70, 1996.

Manoharan et al., Histochemical analysis of biological tissues using Raman spectroscopy. *Spectrochimica Acta Part A,* 52:215–249, 1996.

Mizuno et al., Near–Infrared Fourier Transform Raman Spectroscopic Study of Human Brain Tissues and Tumors. *Journal of Raman Spectroscopy,* 25:25–29, 1994.

Redd et al., Raman Spectroscopic Characterization of Human Breast Tissues: Implications for Breast Cancer Diagnosis. *Applied Spectroscopy,* 47(6):787–791, 1993.

Williams et al., A Critical Comparison of Some Raman Spectroscopic Techniques for Studies of Human Stratum Corneum. *Pharmaceutical Research,* 10(11):1642–1647, 1993.

Williams et al., Comparison of Fourier Transform Raman Spectra of Mammalian and Reptilian Skin. *Analyst,* 119:563–566, 1994.

Zeng et al., Novel miscrospectrophotometer and its biomedical applications. *Optical Engineering,* 32(8):1809–1814, 1993.

Zeng, Human Skin Optical Properties and Autofluorescence Decay Dynamics. Ph.D. Thesis, The University of British Columbia, Vancouver, Canada, 1993.

Duboc et al., Evidence of mitochondrial impairment during cardiac allograft rejection, Transplantation Nov., 1990, 50(5), pp. 751–755.*

Graham et al., Fluorescence of damaged myocardium in endomyocardial biopsy specimens for the evaluation of cardiac transplantation, Hum Pathol Nov. 1985, 16(11), pp. 1110–1114.*

* cited by examiner

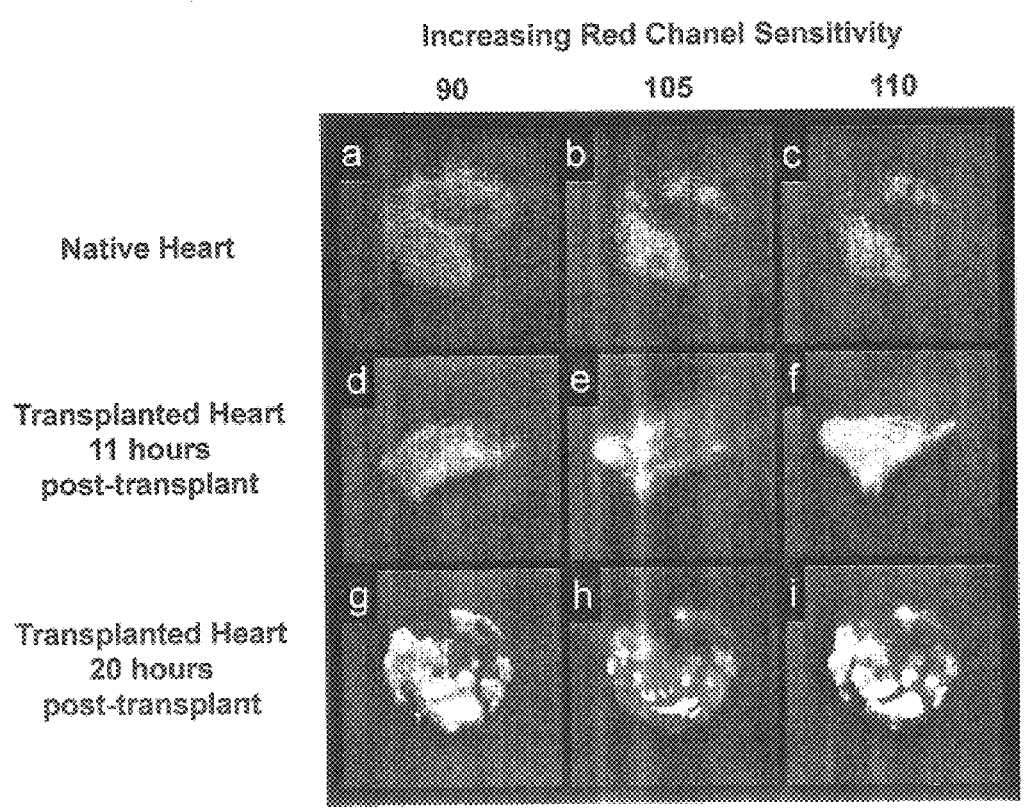
Figure 8  Endoscopic cardiac laser induced fluorescence.

Figure 24(a-e)
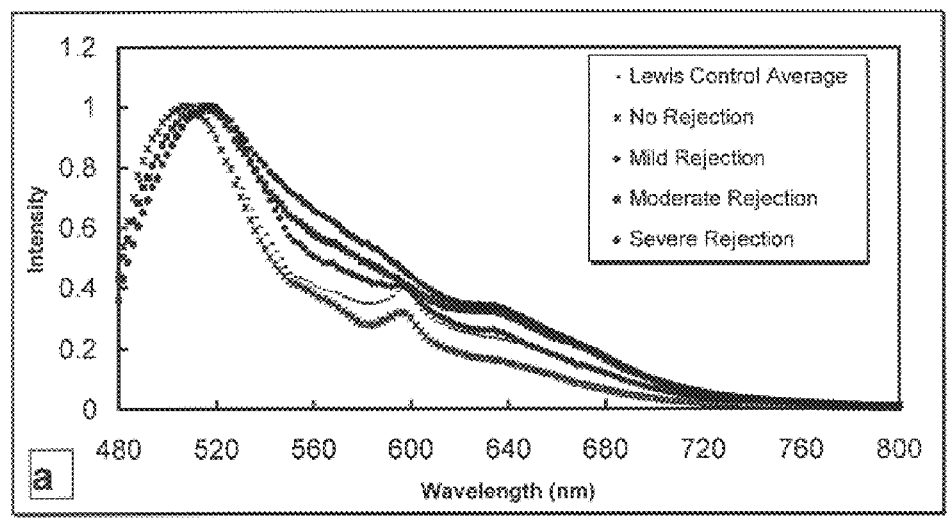
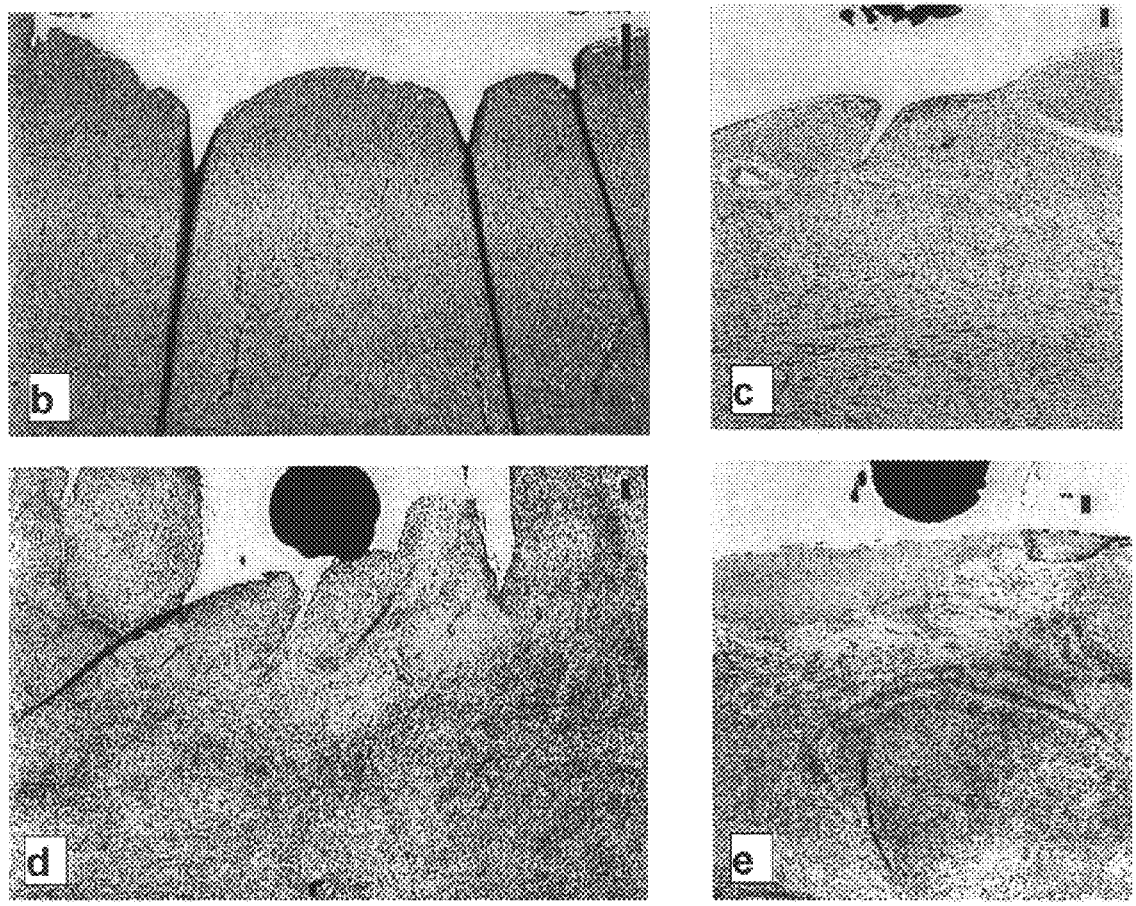

METHODS AND APPARATUS FOR DETECTING THE REJECTION OF TRANSPLANTED TISSUE

CROSS-REFERENCE TO RELATED APPLICATIONS

This application claims priority from U.S. provisional patent application Ser. No. 60/040,557, filed Mar. 13, 1997, U.S. provisional patent application Ser. No. 60/046,368, filed May 15, 1997, U.S. provisional patent application Ser. No. 60/062,512, filed Oct. 16, 1997, U.S. provisional patent application Ser. No. 60/068,693, filed Dec. 23, 1997, all of which are presently pending.

TECHNICAL FIELD OF THE INVENTION

The present invention relates to methods of detecting the possible rejection of transplanted tissue, such as a transplanted organ. The present invention also relates to apparatus for detecting such rejection, and methods relating to such apparatus.

BACKGROUND OF THE INVENTION

The transplanting of tissues such as organs is a well recognized technique in surgery. Unfortunately, a major, long-standing difficulty is the rejection of the transplanted tissue by the host. Briefly, the immune system of the host recognizes a foreign body (i.e., the transplanted tissue) and then rejects that foreign body. A variety of techniques exist for the suppression of rejection, and improved rates of success are now being achieved. A popular technique is to suppress the recipient's immune system, for example with cyclosporin. However, such immunosuppression techniques carry risks for the patient, and are therefore minimized, when possible, by attempting to determine prior to immunosuppression if the tissue exhibits characteristics of rejection.

A standard means of determining whether an organ is being rejected is the conduction of physical biopsies (such as an endomyocardial biopsy (EMB) for the heart). In the case of heart transplants, accurate diagnosis is vital for the effective care of the heart transplant, and percutaneous transvenous EMB is a standard method for such assessment of rejection. Crudely described, this means inserting a catheter comprising a device known as a bioptome, which comprises a wire with tiny jaws at the distal end, into a blood vessel. Many varieties of catheters and bioptomes are known in the art. See, e.g., U.S. Pat. No. 3,964,468; U.S. Pat. No. 4,953,559; U. S. Pat. No. 4,884,567; U.S. Pat. No. 5,287,857; U.S. Pat. No. 5,406,959; WO 96/35374; WO 96/35382; WO 96/29936; WO 96/35374. The distal end of the catheter is fed into an entry point, typically on the leg or neck, and then on to the heart chamber where a tiny piece of tissue is clamped in the jaws of the bioptome and removed for analysis.

This biopsy permits accurate detection of the presence and the severity of histologic changes in the transplanted tissue once the site of rejection is found. In particular, the heart material obtained from the biopsy is graded for the level or severity of the rejection. The International Society for Heart and Lung Transplantation (ISHLT), Kolbeck et al., *Transplant Pathology*, p. 200 (Am. Soc. Clin. Path., 1994), rates cardiac rejection as follows:

TABLE 2

| International Society for Heart and Lung Transplantation | |
|---|---|
| Grade 0 | No evidence of acute rejection |
| Grade 1 | Mild |
| | A. Focal/Perivascular |
| | B. Diffuse/Interstitial |
| Grade 2 | Moderate, Uni-focal |
| Grade 3 | Moderate, Multi-focal |
| | A. Several foci |
| | B. Diffuse |
| Grade 4 | Severe |
| | Ongoing |
| | Mild, moderate, severe |
| | Resolving |

In an alternative formulation, Billingham's Histopathologic Classification of Rejection, Kolbeck et al., *Transplant Pathology*, p. 199 (Am. Soc. Clin. Path., 1994), establishes the features of tissue rejection as follows:

TABLE 3

| Billingham's Histopathologic Classification of Acute Rejection in Human Heart Allograft | | |
|---|---|---|
| Severity of Acute Rejection | Features | Prognostic and Implications Therapeutic |
| Mild | Rare (usually 1–2) localized perivascular collections of mononuclear cells with limited extension into the interstitium. No definite myocardial injury. | Reversible, typically without augmentation of immunosuppressive therapy. |
| Moderate | Collection of "activated" perivascular and interstitial mononuclear cells with associated myocyte injury. | Reversible, typically with augmentation of therapy and rebiopsy. |
| Severe | Widespread inflammatory infiltrates including mononuclear cells and often polymorphonuclear leukocytes and eosinophils. Multifocal tissue and small vessel necrosis is associated with fresh hemorrhage. | Reversible, but with difficulty. Requires augmentation of therapy. |
| Resolving | Granulation tissue at various stages if collagenization. Includes numerous fibroblasts with scattered mononuclear cells, plasma cells and phagocytosed lipochrome pigment. | Reversed rejection, spontaneously or therapeutically induced. |

A patient may require an average of 5 and as many as 10 biopsies per biopsy procedure. Thus, over the first year of a heart transplant recipient, as many as 180 EMBs are taken. A typical schedule for EMBs is as follows:

TABLE 1

Right Ventricular Biopsy Protocol for Heart Transplant

| Period | Time | Frequency | Procedures |
|---|---|---|---|
| Immediate post-operative | 0–4 weeks | from day five, twice weekly | 6 |
|  | 4–6 weeks | weekly | 3 |
| Late post-operative | 2–3 months | bimonthly | 4 |
|  | 4–6 months | monthly | 3 |
|  | 6–12 months | quarterly | 2 |
| Total | First Year |  | 18 |
|  | After one year | yearly (in the absence of rejection) |  |
| After rejection therapy |  | 14–21 days |  |

EMBs, and other biopsies, are problematic, however, because during each biopsy a number of potential complications may occur. These complications include the following:

right ventricular perforation cardiac tamponade ventricular and supraventricular arrhythmia embolus (thrombus or air)

pneumothorax air in the pleural cavity infection bleeding

EMBs are the principle method for monitoring cardiac allograft rejections.

Thus, the EMB, which is a physical biopsy and diagnostic aid, is hazardous for the patient. Attempts have been made to reduce the number of biopsies per patient, but these attempts have not been successful, due in part to the difficulty in pinpointing the sites where rejection starts and to the difficulty in assessing tissue without performing the actual biopsy.

Accordingly, there has gone unmet a need for methods and apparatus that reduce the number of EMBs that a patient must suffer subsequent to undergoing a transplant procedure. There has also gone unmet a need for methods and devices that assist in pinpointing sites where rejection starts. The present invention provides these and other related advantages.

SUMMARY OF THE INVENTION

The present invention provides methods of, and apparatus for, detecting the possible rejection of transplanted tissue, such as a heart, by a host. Generally, the methods comprise subjecting the tissue to ultraviolet to visible light illumination, collecting the fluorescence light induced by the illumination to permit analysis, and comparing the results from the transplanted tissue to results for known tissue, typically healthy tissue; the fluorescence from tissue having characteristics of rejection is different from the fluorescence from healthy tissue.

Accordingly, in one aspect the present invention provides methods for determining whether a transplanted tissue comprises one or more characteristics indicative of rejection by a host. The methods comprise a) illuminating the transplanted tissue under conditions suitable to cause the transplanted tissue to fluoresce; b) collecting the fluorescence to provide a transplant fluorescent signature; and c) comparing the transplant fluorescent signature with a known fluorescent signature representative of the same type of tissue as the transplanted tissue, and therefrom determining whether the transplanted tissue exhibits one or more characteristics indicative of rejection.

In a preferred embodiment that relates to this and other aspects of the present invention (which is so for other preferred embodiments unless a given aspect of the invention indicates that such embodiment does not apply to that aspect), the transplanted tissue is illuminated with light that does not comprise UV light, further preferable light that consists essentially of blue light, even further preferably light that consists essentially of a wavelength of about 442 nm.

In another preferred embodiment, methods are implemented using a catheter or endoscope that comprises at least one illumination light guide that conducts light to the transplanted tissue to illuminate the transplanted tissue and at least one collection light guide that collects fluorescence from the transplanted tissue, and the methods further comprise collecting a plurality of transplant fluorescence signatures preferably without substantially moving the catheter or endoscope relative to the transplanted tissue, wherein at least two of the plurality of transplant fluorescence signatures comprise a significant fluorescence contribution from a plurality of selected different depths of the transplanted tissue to provide at least two different fluorescence signatures. Preferably, the catheter or endoscope comprises at least a first collection light guide and a second collection light guide each of which is spaced a different distance from its associated illumination light guide, and the collection of the at least two different fluorescence signatures comprises collecting light using each of the first collection light guide and the second collection guide during the collecting steps. In one preferred embodiment, the illumination light guide associated with each of the first collection light guide and the second collection light guide is a single light guide.

In a further preferred embodiment, the step of illuminating comprises illuminating the tissue using light from an illumination light guide, and the step of collecting comprises collecting the fluorescence in a collection light guide.

In another embodiment of the present invention, the steps of illuminating and collecting are performed during a single diastole. Such steps can be initiated using one or more signals of an electrocardiogram, a blood pressure pulse of the host, preferably measured using a blood pressure monitor located externally to the host such as a pulse oximeter.

In still a further embodiment of the present invention, the step of comparing comprises comparing one or more of the full width at half maximum (FWHM) of the transplant fluorescent signature with the known fluorescent signature, the ratio of the integrated intensity of two or more wavelength bands of the transplant fluorescent signature with the known fluorescent signature, which can be measured by broad band optical detectors and wherein the method can further comprise selecting a specific spectral region using an optical band pass filter, and the wavelength of maximum intensity of the transplant fluorescent signature with the known fluorescent signature.

Preferably, the tissue is illuminated and the fluorescence is collected in vivo.

In another aspect, the present invention provides methods of determining the orientation of an optical probe relative to a target tissue. The optical probe comprises at least one light emitter and at least three light collectors that are equally radially distanced from the at least one light emitter, and the method comprises the following steps: a.) emitting light from the at least one light emitter to the target tissue under conditions suitable to cause light to emanate from the target tissue; b.) collecting the emanating light entering the at least three light collectors; and, c.) measuring the relative intensity of the emanating light collected by each of the at least three light collectors, and therefrom determining the orientation of the optical probe with respect to the target tissue.

In a further aspect, the present invention provides methods of determining the orientation of an optical probe relative to a target tissue wherein the optical probe comprises at least three pairs of light guides comprising a light emitter and a light collector, a light emitter equally distanced from a light collector in each of the three pairs. The methods comprise the following steps: a.) emitting light from each of the at least three light emitters to the target tissue under conditions suitable and for a time sufficient to cause light to emanate from the target tissue; b.) collecting the emanating light entering the at least three light collectors; and, c.) measuring the relative intensity of the emanating light collected by each of the at least three light collectors, and therefrom determining the orientation of the optical probe with respect to the target tissue.

In yet another aspect, the present invention provides methods for determining whether a target tissue exhibits one or more characteristics indicating that the target tissue be biopsied. The methods comprise: a.) removably attaching an optical probe comprising at least one light emitter and at least one light collector to a target tissue in vivo; b.) emitting light from the at least one light emitter to the target tissue under conditions suitable to cause light to emanate from the target tissue; c.) collecting the emanating light entering the at least one light collector; and, d.) evaluating the emanating light to determine whether the target tissue exhibits one or more characteristics indicating that the target tissue be biopsied.

In a preferred embodiment, the methods further comprise obtaining the biopsy if the target tissue comprises the characteristics indicating that the target tissue be biopsied; further preferably, the optical probe is positioned at a distal end of a catheter or endoscope having a bioptome, the step of attaching comprises removably attaching the bioptome to the target tissue, and the step of obtaining the biopsy comprises closing the bioptome to obtain a portion of the target tissue.

In another preferred embodiment, the optical probe is a part of a catheter or endoscope system, the system comprising a catheter or endoscope comprising a light source at a proximal end and the optical probe at a distal end, and wherein the light emitter is an illumination light guide that transmits light from the light source to the distal end and the light collector is a collection light guide that transmits the emanating light from the distal end to the proximal end of the catheter. Further preferably, as noted above, the illumination light guide and the collection light guide consist of a single light guide.

In still yet another aspect, the present invention provides methods for determining whether a target tissue exhibits one or more characteristics indicating that the target tissue be biopsied, the methods comprising: a.) placing an optical probe adjacent to the target tissue, the optical probe comprising at least one light emitter and at least three light collectors that are equally radially distanced from the at least one light emitter; b.) emitting light from the at least one light emitter to the target tissue under conditions suitable to cause light to emanate from the target tissue, to provide emanating light; c.) collecting the emanating light entering the at least three light collectors; d.) measuring the relative intensity of the light collected by each of the at least three light collectors, and therefrom determining an orientation of the optical probe with respect to the target tissue; and e.) determining whether the orientation is adequate to provide sufficient to indicate that the target tissue exhibits the one or more characteristics indicating that the target tissue be biopsied.

In still yet a further aspect, the present invention provides methods for determining whether a target tissue exhibits one or more characteristics indicating that the target tissue be biopsied, the methods comprising: a.) placing an optical probe adjacent to the target tissue, the optical probe comprising at least three pairs of light emitters and light collectors, the light emitter equally distanced from the light collector in each of the three pairs; b.) emitting light from each of the at least three light emitters to the target tissue under conditions to cause light to emanate from the target tissue, to provide emanating light; c.) collecting the emanating light entering the at least three light collectors; d.) measuring the relative intensity of the light collected by each of the at least three light collectors, and therefrom determining an orientation of the optical probe with respect to the target tissue; and e.) determining whether the orientation is adequate to provide data sufficient to indicate that the target tissue exhibits the one or more characteristics indicating that the target tissue be biopsied.

In preferred embodiments, the target tissue is transplanted tissue and the one or more characteristics indicating that the target tissue be biopsied comprise one or more characteristics of rejection by a host containing the target tissue.

In other preferred embodiments, the host is a human, although the host can be any selected animal, such as a cow, horse, sheep, dog, cat, pig or fowl. In further preferred embodiments, at least one step of the methods is computer implemented; all steps can be computer implemented if desired.

Turning to still other aspects, the present invention provides catheter and endoscope systems comprising a light source that supplies light at a proximal end of a catheter, at least one illumination light guide suitable for conducting light from the proximal end to a distal end of the catheter and for emitting the light from a distal end of the illumination light guide, at least one collection light guide suitable for collecting light entering the distal end of the collection light guide and conducting the light to the proximal end of the catheter, and a bioptome. In a preferred embodiment, as noted above, the illumination light guide and the collection light guide are the same light guide, such as a single optic fiber.

In another aspect, the present invention provides catheter systems suitable for emitting and collecting light, the catheter systems comprising a light source that supplies light at a proximal end of a catheter, at least one illumination light guide suitable for conducting light from the proximal end to a distal end of the catheter and for emitting the light from a distal end of the at least one illumination light guide, and at least three collection light guides, each collection light guide suitable for collecting light entering the distal end of the collection light guide and conducting the light to the proximal end of the catheter, wherein the collection light guides are equally radially disposed around the at least one illumination light guide.

In still another aspect, the present invention provides catheter systems suitable for emitting and collecting light, the catheter systems comprising a light source that supplies light at a proximal end of a catheter, at least three pairs of light guides, each pair comprising an illumination light guide suitable for conducting light from the proximal end to a distal end of the catheter and for emitting the light from a distal end of the illumination light guide and a collection light guide suitable for collecting light entering the distal end of the collection light guide and conducting the light to the proximal end of the catheter, and wherein the distance from the collection light guide to the illumination light guide is equal in the at least three pairs.

In still a further aspect, the present invention provides catheter and endoscope systems suitable for emitting and collecting light, the catheter or endoscope comprising at least one light source that supplies light at a proximal end of the catheter and a plurality of light guides, wherein at least two of the light guides are suitable for emitting and collecting light at different sites located along a distal end of the catheter or endoscope, such that the catheter or endoscope is capable of emitting and collecting light at a number of different sites along the distal end of the catheter or endoscope without moving the distal end.

Preferably, the catheter and endoscope systems are operably linked to a computer containing at least one computer implemented program able to perform at least one of determining a spectrum of light collected by the collection light guide, determining an intensity of light collected by the collection light guide, comparing the relative intensity of light collected by a plurality of collection light guides and timing light to be one or both of transmitted or collected along the light guides in concert with a pulse or electrocardiogram.

In still yet another aspect, the present invention provides methods implemented using the catheter and endoscope systems described herein.

These and other aspects of the present invention will become evident upon reference to the discussion herein and the attached drawings. In addition, various references are set forth herein that describe in more detail certain procedures or apparatus, etc. (e.g., bioptomes, fluorescence technology, etc.); all such references are incorporated herein by reference in their entirety.

BRIEF DESCRIPTION OF THE DRAWINGS

FIG. 8 depicts an endoscopic cardiac laser induced fluorescence.

FIGS. 24a–24e comprise a graph depicting spectral changes corresponding to the presence of no rejection, mild rejection, moderate rejection and severe rejection in cardiac tissue, along with exemplary photographs of H&E stained sections corresponding to such autofluorescence spectra.

DETAILED DESCRIPTION OF THE INVENTION

Figure 1:
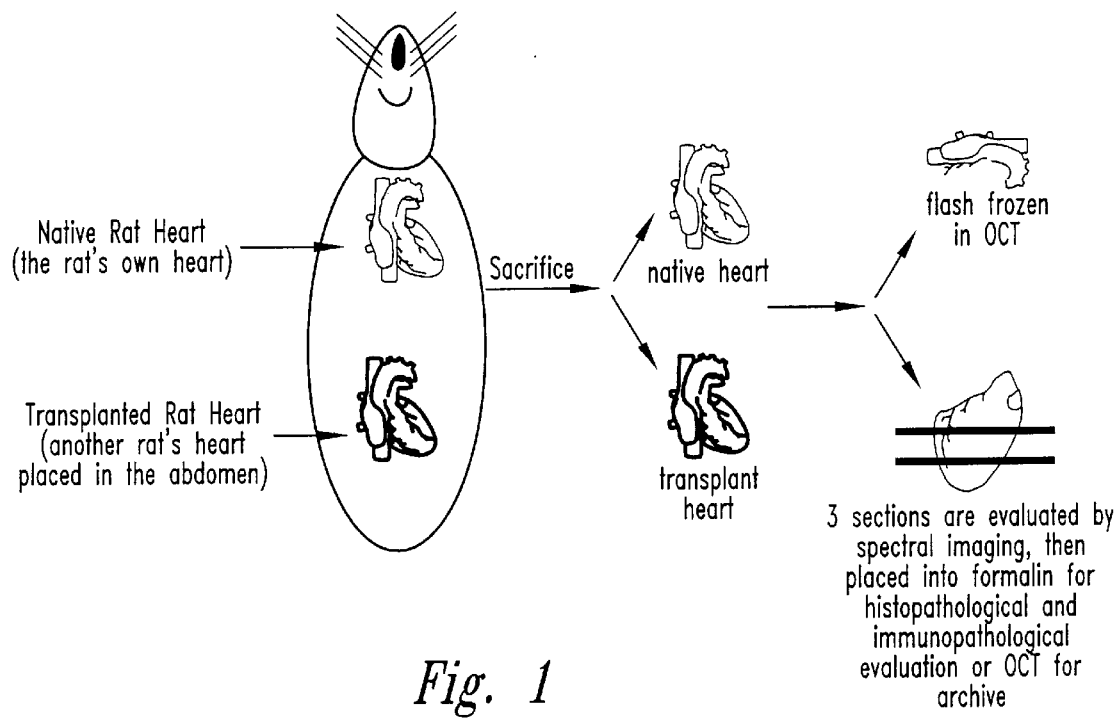
FIG. 1 is a schematic representation of a rat heart transplant procedure, as discussed in Example 1.

Healthy tissue exhibits a characteristic fluorescence response in reply to excitation with ultraviolet to visible light. The present inventors have discovered that the fluorescence response of transplanted tissue changes as the transplanted tissue is rejected by the host organism. Thus, the present invention provides methods and apparatus suitable for measuring changes in the fluorescence properties, and other related properties such as Raman responses, and therefore the presence of characteristics of rejection, of transplanted tissue, both in vitro and in vivo. Detection of such characteristics of rejection assist in determining whether a tissue biopsy is needed in a transplanted organ, and therefore can eliminate needless biopsies to the benefit of the patient. Such detection also assists in selecting sites within an organ for tissue biopsies for pathological analysis.

In order to provide these features, the present invention provides methods for the detection of tissue rejection comprising inducing and analyzing fluorescence of transplanted tissue, as well as methods related to induction and analysis of fluorescence generally. The present invention also provides apparatus, including catheter and endoscope systems and catheters and endoscopes, comprising optical probes and/or bioptomes that are particularly suited for such induction and analysis (the discussion herein relating to catheters applies equally to endoscopes unless the context clearly indicates otherwise). The apparatus can also be used for purposes other than the detection of tissue rejection, if desired, and thus the present invention also provides methods related to the use of the apparatus described herein that include uses other than the detection of rejection of transplanted tissue.

Thus, in one aspect the present invention provides methods for determining whether a transplanted tissue comprises one or more characteristics indicative that the tissue is undergoing rejection by its recipient host. A transplanted tissue is a tissue such as an organ such as the heart, liver, kidney, skin, or lungs that has been transferred from a first, donor organism or a synthetic source such as a tissue culture (e.g., for blood or skin) to a second, donee organism (also referred to as a host or recipient). The transplant can be from any combination of donor and donee organisms or sources, including homogeneic, syngeneic, allogeneic or heterogeneic organisms. The transplanted tissue exhibits or comprises one more characteristics indicative of rejection by the host when the tissue appears to suffer at least Grade 1 or mild rejection as discussed in the Tables above. In a preferred embodiment, where the transplanted tissue exhibits characteristics indicative of rejection, the method further comprises determining the level of rejection, which can be correlated to the grades and/or levels discussed in the Tables above.

In one embodiment that is particularly preferred for the induction of fluorescence (which can also be used with other methods of the present invention), the methods comprise transmitting light comprising light from about ultraviolet light to about visible light to illuminate the transplanted tissue under conditions suitable to cause the transplanted tissue to fluoresce, collecting the fluorescence (limited to a certain temporal window of the fluorescence if desired), preferably at a plurality of wavelengths, to provide a transplant fluorescent signature, and comparing the transplant fluorescent signature with a fluorescent signature that is representative of tissue that is the same type of tissue as the transplanted tissue, and therefrom determining whether the transplanted tissue exhibits one or more characteristics of rejection. The representative fluorescence signature, defined herein as a known fluorescence signature, that is used for comparison is preferably of healthy tissue, but it can also be from tissue exhibiting a known rejection response (or other known characteristic for certain embodiments of the invention).

Transmitting the light to the transplant tissue comprises delivering light from a light source (such as a lamp) to the tissue. As discussed further below, the light is typically transmitted by a light guide, such as an optical fiber, fiber bundle, liquid light guide or hollow reflective light guide or lens system.

The light that is transmitted to the transplanted tissue (or other target tissue for other aspects of the invention) typically comprises light from ultraviolet light through visible light and can induce fluorescence or other desired response in the transplant tissue. Preferably, and particularly where the methods are implemented in vivo, the light does not comprise UV light because such light can be harmful to the tissue. Further preferably for embodiments that entail the induction of fluorescence, the light consists essentially of blue light, and even further preferably light of a wavelength of about 430 nm–450 nm. Preferred specific wavelengths include about 405 nm, 436 nm and/or 442 nm+/–about 5 nm. In alternative embodiments, such as where the detection comprises the determination of a Raman spectra, the light consists essentially of infrared light, further preferably a specific, desired wavelength corresponding to a desired Raman band or other wavelength appropriate for the selected detection method.

Where the examination of the tissue comprises induction of fluorescence, the light is transmitted to the transplanted tissue under conditions to excite or cause the transplanted tissue to fluoresce. Conditions to induce fluorescence in tissue are well known in the art. See, e.g., U.S. Pat. No. 4,836,203; U.S. Pat. No. 5,042,494; U.S. Pat. No. 5,062,428; U.S. Pat. No. 5,071,416; U.S. Pat. No. 5,421,337; U.S. Pat. No. 5,467,767; U.S. Pat. No. 5,507,287. Fluorescence and fluoresce are used herein in their ordinary sense, which includes the emission of, or the property of emitting, electromagnetic radiation, typically in the visible wavelength range, resulting from and occurring following the absorption of the light that is transmitted to the transplanted tissue as a part of the method. Fluorescence includes fluorescent light produced by either endogynous fluorophores or exogynous fluorophores; exogynous fluorophores include those provided by drugs, chemical labels or other external sources. Autofluorescence is fluorescence from endogynous fluorophores. The fluorescence is collected, or gathered, from the transplanted tissue so that it can be analyzed to provide a transplant fluorescent signature, which means a particular fluorescent spectral emission for that particular transplanted tissue. Preferably, the fluorescence is collected at a plurality of wavelengths to facilitate analysis of the transplant fluorescent signature. For example, the collection and analysis of a plurality of wavelengths permits observation of a change of intensity from one wavelength to another. The transplant fluorescent signature is then compared with a known, preferably healthy, fluorescent signature, which means a fluorescent signature that represents tissue that is preferably the same type of tissue as the transplant tissue (e.g., the signature for a transplanted human heart is compared to the signature for a human heart wherein the tissue has known status, which is preferably healthy but could be, for example, grade I, II, III or IV rejection). If the transplant fluorescent signature is similar to a healthy fluorescent signature, then the transplanted tissue does not comprise, or exhibit, characteristics of rejection. Thus, a biopsy is typically not needed for the transplanted tissue, and therefore the scanning of the transplanted tissue using the methods of the present invention prevents the unnecessary extraction of tissue from the transplanted tissue, along with the attendant risks discussed above. If the transplant fluorescent signature shows one or more indicia of rejection, such as a red-shift relative to the healthy fluorescent signature, then the transplanted tissue comprises characteristics of rejection, and further action, typically including a biopsy, should be taken.

Fluorescence characteristics that contribute to the changes observable in transplanted tissue undergoing rejection are affected by the wavelength of excitation, the concentration, absorption coefficients, scattering coefficients, quantum efficiency, and the emission spectra of the fluorophores inside the tissue. For example, in vivo determination of the presence or absence of characteristics of rejection of a transplanted heart preferably includes measurement and analysis at the endocardium, epicardium, myocardium and/or arterial tissue of the fluorescence characteristics described above, as well as changes in fluorescence characteristics due to physiological changes associated with rejection such as thickening of the endothelium and increase in collagen content.

Different wavelengths of illumination or excitation light can excite different fluorophores inside the transplanted tissue, and therefore can lead to different quantum efficiencies for exciting tissue fluorescence. Thus, the user can select one or more desired excitation wavelengths in order to achieve better or more complete detection sensitivity. In one preferred embodiment, a Laser/Spectrometer system is used for various excitation wavelengths because such a system conveniently facilitates utilizing excitation wavelengths from about 360 UV nm to about 700 IR nm.

In addition to using different wavelengths of illumination light, multiple wavelengths of illumination light can be used simultaneously or sequentially, thereby providing at least two photons of different wavelengths for absorption by the transplanted tissue. For example, combining simultaneous excitation by one photon at 400 nm with excitation by a second photon at 500 nm can provide enhanced detection because the long wavelength light can penetrate deeper into the tissue to sample a large tissue volume. In addition, different fluorophores may be excited, and the absorption of the fluorescence spectra by interfering matter can be reduced.

In one preferred embodiment, the induction of fluorescence comprises the simultaneous excitation of the fluorophore by multiple photons, each having a certain fraction of the energy of a single photon at the desired excitation wavelength. In particular, when the multiple photons (which are of a longer wavelength) simultaneously contact the fluorophore, the energies of the photons combine to provide the same excitation that is achieved by the use of the wavelength. An advantage of this approach is that the longer wavelength, lower energy photons can penetrate deeper into the tissue, and therefore sampling can take place at different and/or deeper tissue depths. Typically, this multi-photon excitation is effected using two photons that each have one-half the energy of the desired photon, although it is possible to use three photons each having one-third the energy, etc. The resulting fluorescence is the same as the fluorescence induced using other excitation methods discussed herein, and therefore the analysis of the fluorescence is also the same. In a preferred embodiment, the illumination light guide(s) comprises a focusing device at its distal end, for example a gradient refractive index (GRIN) lens, a microlens, or a diffractive optic lens.

The spectroscopic analysis herein can comprise comparing a full width at half maximum (FWHM) of the measured fluorescence spectrum that comprises the transplant fluorescent signature with a FWHM of the fluorescence spectrum that comprises a healthy fluorescent signature characteristic of healthy tissue when the healthy tissue is the same type of tissue as the transplant tissue. Examples of spectroscopic analyses are shown in FIGS. 5a through 7b. The FWHM is the full width of the measured fluorescence spectrum at a level that is one-half the maximum height of the spectrum.

The spectroscopic analysis can alternatively, or also, comprise comparing the ratio of the integral intensity of two or more wavelength bands of the spectrum that comprises the transplant fluorescent signature to the same ratio from healthy tissue. The wavelength bands for such an analysis can be selected, for example, by using numerical techniques to select sub-regions from the measured fluorescence spectrum acquired with a spectrometer or by using optical techniques, for example optical band pass filters, to select specific spectral bands that are measured by broadband optical detectors. Thus, a wavelength band is a range of wavelengths of light defined by a selected shorter wavelength limit and a selected longer wavelength limit. In some embodiments, the wavelength band is measured by a broad band optical detector, which are characterized by a response to light across a broad spectral region, typically greater than several hundred nanometers. Examples of broad band detectors include silicon detectors, photomultiplier tubes (PMTs) and CCD assays. Additionally, the wavelength bands can be specific spectral bands, which can be selected using optical band pass filters in conjunction with the broad band detector.

As another alternative, the step of comparing can comprise comparing the wavelength of maximum intensity of the fluorescence spectrum of the transplanted tissue with the wavelength of maximum intensity of the fluorescence spectrum from the healthy tissue. The wavelength of maximum intensity is the wavelength at which the fluorescent spectrum reaches its maximum intensity; a red-shift in the wavelength of maximum intensity indicates that the transplanted tissue comprises characteristics of rejection.

In a preferred embodiment that applies to this and other aspects of the invention, the step of collecting comprises selectively collecting a significant portion, preferably at least about 10%, of the collected fluorescence or other induced response from an approximately 0.05–0.2 mm thick segment of the transplanted or other target tissue, the segment being located anywhere at a depth from 0–1 mm below the surface of the transplanted tissue. Preferably, at least about 70% of the fluorescence is collected at such level, and further preferably at least about 85% of the fluorescence is collected at such level. Additionally, in alternative embodiments, the fluorescence is collected within a segment that is at a depth of about 0.05–0.3 mm, preferably at about 0.05–0.15 mm, and further preferably at about 0.1–0.2 mm. The depth of the selected segment from the surface of the transplanted tissue is determined by measuring perpendicularly from the center of the distal tip of the optical probe where it contacts, or is nearest to, the target tissue.

Figure 13A:
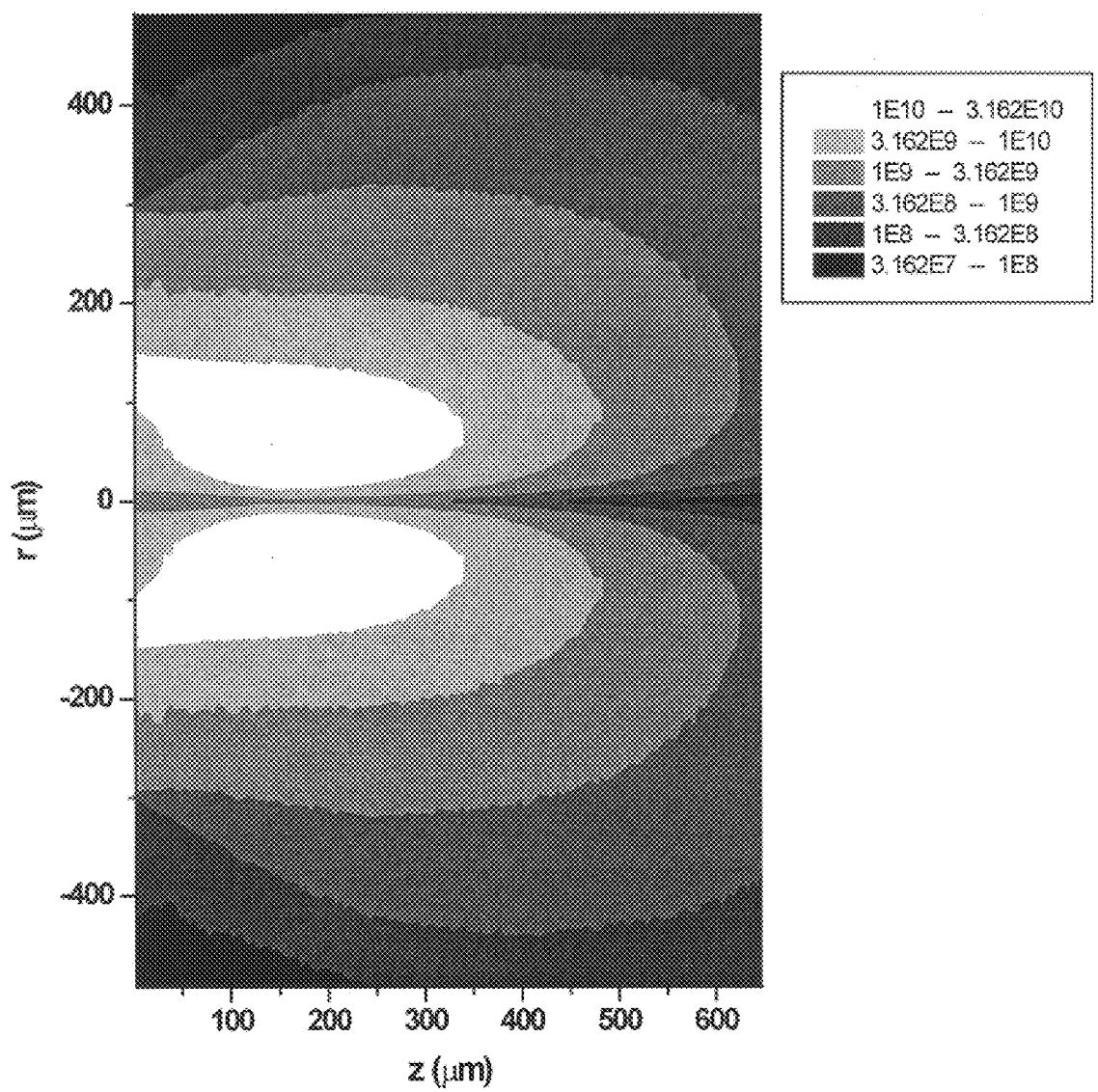
FIGS. 13a and 13b depict two Monte Carlo Simulations depicting the depth of fluorescence induction and pickup using traditional excitation methods.
Figure 13B:
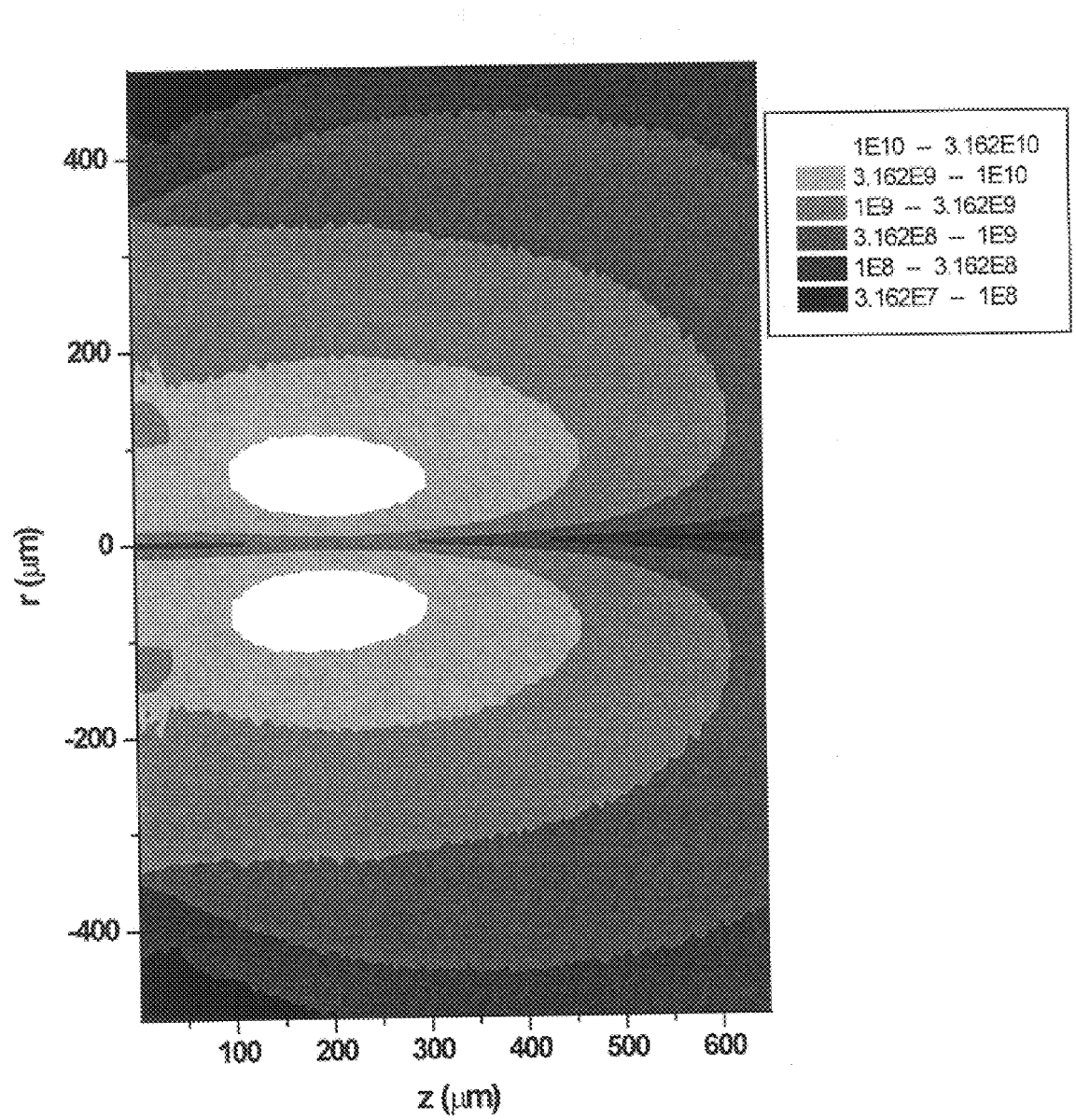

An example of the induction of fluorescence in different depth segments of a target tissue is set forth in FIGS. 13a–13b. In FIG. 13, the graphs are contour plots based on a Monte-Carlo calculation of the probe's sensitivity to the tissue area near its tip (the probe tip has a single illumination light guide centrally disposed among six surrounding collecting light guides, as in FIG. 15). The value at a particular r and z is the contribution from the volume element generated by rotating the square grid element in the r–z plane about the r=0 axis (volume~$2\pi r \Delta r \Delta z$). In FIG. 13a, the collection fibers are hypothetically disposed immediately adjacent to the excitation light guide (and therefore extend from +100 $\mu$m to +300 $\mu$m and −100 $\mu$m to −300 $\mu$m, respectively). In FIG. 13b, a hypothetical 50 $\mu$m thick cladding/spacer encompasses the centrally located excitation light guide, and therefore the collection light guides extend from +150 $\mu$m to +350 $\mu$m and −150 $\mu$m to −350 $\mu$m. As can be seen by the key to the right of the graphs, the different graph areas represent different ranges of sensitivity.

The contours are spaced on a logarithmic scale (arbitrary units) with each level representing a half-decade.

As can be seen from FIG. 13b, the highest level of contribution to the collected fluorescence (assuming a uniform distribution of fluorophores inside the tissue) occurs in the region from about 100 μm to 300 μm deep and at a radial distance of 30 μm to 100 μm. The equivalent region in FIG. 13a is much larger and extends all the way to the tissue surface where the probe tip is situated. As a result, a higher percentage (23%) of the total signal for FIG. 13a would originate in the first 100 μm below the tissue surface as compared to FIG. 13b (17%). Similarly, only 12% of the total signal in FIG. 13b comes from the region from 400 μm to 650 μm whereas 17% comes from this region in FIG. 13a. This percentage increases to 21% from this region for the case where there is a 100 μm thick space between illumination and collection fibers. Thus, by varying the separation between illumination and collection fibers, sensitivities to different depths in the tissue can be obtained. It is also possible to change the depth sensitivity by changing the relative size of the collection and emission fibers or by adopting a different arrangement for the collection/ illumination array (e.g., a linear array as opposed to a concentric one).

Catheters or endoscopes that are useful for detection of the indicated characteristics at different depths in the transplanted tissue (or other tissue when appropriate), can be made by providing at least one illumination light guide and a plurality of collection light guides, wherein the collection light guide(s) and the illumination light guides are spaced at differing distances from one another. For example, a single illumination light guide can be centrally disposed within the distal tip of the catheter or endoscope and a plurality of collection light guides can be disposed in a radial spiral away from the illumination light guide. Alternatively, the illumination light guide and the plurality of collection light guides can be maintained in a line, or the distal tip can comprise a plurality of illumination light guides and collection light guides in a geometric matrix, or in a random or semi-random matrix, such that selection of differing illumination light guides and collection light guides allows for differing distances between the light guides; such an arrangement can be preferable for some purposes because the plurality of illumination light guides provides for implementation of multiple light sources.

In a further aspect, the present invention provides methods of determining the orientation of an optical probe relative to a target tissue. The orientation of the optical probe means the angle and/or distance of the optical probe in comparison to the target tissue. The target tissue can be transplanted tissue as discussed above, or the target tissue can be any other tissue for which examination with an optical probe would be advantageous. The optical probe is a probe capable of transmitting light bi-directionally, and of emitting and gathering light, and is preferably a probe disposed at the distal end of a catheter or endoscope and therefore suitable for insertion and use within a living body. As is well known in the art, a catheter or endoscope is a generally tubular device for insertion into a body, typically via canals, vessels, passageways or body cavities for any of a variety reasons, including the diagnostic purposes such as those described herein as well as other purposes such as the injection or withdrawal of fluids or to keep a passageway open. The distal end of a catheter or endoscope is the end of the catheter or endoscope that is inserted into the body and directed to a target tissue; the proximal end is the end of the catheter or endoscope that is maintained outside the body, and typically comprises one or more handles, knobs and/or other control devices that allow the user to manipulate the distal end of the catheter and/or devices located at the distal end of the catheter or endoscope. As used herein, the distal end of the catheter or endoscope includes the distal tip of the catheter or endoscope, which is the most distal surface or opening of the catheter or endoscope, and the portion of the catheter or endoscope adjacent to the distal tip of the catheter or endoscope.

Figure 15:
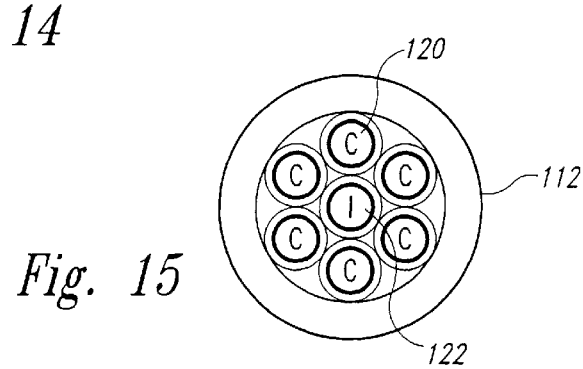
FIG. 15 is a schematic drawing of the distal end of an optical probe suitable for determination of the orientation of the probe to a target tissue.

In one embodiment, the optical probe of the invention comprises at least one light emitter, which means a device capable of launching light from the optical probe, and at least three light collectors (preferably six), which means devices that are capable of gathering light that strikes a receptive window of the light collector. The at least three light collectors are preferably equally radially distanced from the at least one light emitter, which typically means that the light emitter(s) is centrally located and the light collectors form a circle around the light collector. One example of such an array is depicted in FIG. 15, and is discussed further below.

The methods of determining the orientation of the optical probe comprise the following steps. Light is emitted, or launched, from the at least one light emitter to the target tissue under conditions suitable to cause light (which can be, for example, reflectance light or fluorescent light) to emanate from the target tissue. Such return light can be termed "emanating light" and means light that is launched from the target tissue. Such emanating light is collected as it enters the at least three light collectors. Collected light is then analyzed to measure the relative intensity of the emanating light collected by each of the at least three radially disposed light collectors, which means the intensity of the emanating light is measured for each of the collection light guides and then assigned a value relative to the other light guides. Equal measurements for each of the collection light guides indicates that the optical probe is perpendicular to the target tissue; variance from equal gives the relative position of the probe. In view of the present disclosures, an artisan of ordinary skill can also vary the radial distance or diameter of one or more of the light collectors from the light emitter(s) and then account for such variation when determining the orientation of the optical probe, and still be within the scope of this discussion. In addition, the overall strength of the emanating light provides information about the distance of the optical probe from the target tissue, and therefore the measurement of the relative intensity of the collected emanating light can also provide a value of the absolute intensity of such light and the distance from optical probe to the target tissue.

In another aspect capable of determining the orientation of an optical probe relative to a target tissue, the present invention provides methods wherein the optical probe comprises at least three pairs of light emitters and light collectors. The light emitter in each of the at least three pairs is equally distanced from the light collector, which means that for each of the pairs, the light available for collection by the light collector is of the same relative intensity when the optical probe is perpendicular to the surface of the target tissue.

Generally, the methods comprise the following steps. Illumination light (typically equal in intensity, wavelength, etc., so that the emanating light induced by the illumination will be equal when the probe is perpendicular to the target tissue) is emitted from each of the at least three light emitters to the target tissue under conditions suitable to cause light to emanate from the target tissue, to provide emanating light.

The emanating light entering the at least three light collectors is collected. And, the relative intensity of the emanating light collected by each of the at least three light collectors is measured, therefrom providing for the determination of the orientation of the optical probe with respect to the target tissue.

In still another aspect, the present invention provides methods relating to a biopsy, which comprises the removal of tissue from the body of a living organism, preferably a human being (human beings are the preferred subjects for each of the aspects and embodiments of the present invention, but the invention can be practiced for the benefit of other animals such as dogs, cats, horses and cows).

Generally, the methods comprise the following steps. An optical probe comprising at least one light emitter and at least one light collector is removably attached to a target tissue in vivo, which means that the optical probe is physically, releasably attached to the target tissue, typically by mechanical devices that can be attached and released at will via the manipulations of a handle, knob or other control mechanism located at the proximal end of a catheter. Light is emitted from the at least one light emitter to the target tissue under conditions suitable to cause light to emanate from the target tissue, to provide emanating light. The emanating light entering the at least one light collector is collected and then evaluated to determine whether the target tissue comprises the one or more characteristics indicating that the target tissue should be biopsied. Such characteristics include characteristics of rejection as discussed above, characteristics of disease such as cancer or bacterial or viral infection, and characteristics of inflammation. If the target tissue comprises one or more characteristics indicating that the tissue may be unhealthy, additional methods further comprise obtaining the biopsy from the target tissue.

In a preferred embodiment, the optical probe is a part of the distal end of a catheter or endoscope that also comprises a bioptome. In one embodiment, the step of removably attaching comprises clamping the jaws of the bioptome (or other cutting mechanism) onto the target tissue, and obtaining the biopsy comprises closing the bioptome about the target tissue, which means closing the bioptome sufficiently to separate, or remove, a piece of the target tissue from the target tissue. Certain preferred embodiments suitable for use for these aspects of the invention are discussed in U.S. patent application Ser. No. 09/039,279, filed Mar. 12, 1998, corresponding PCT application publication no. WO 98/40015, and entitled Catheters and Endoscopes Comprising Optical Probes and Bioptomes and Methods of Using the Same.

In another preferred embodiment, the optical probe is a part of a catheter or endosocope system, which means at least a catheter capable of conducting light back and forth from its proximal end and its distal end, and a light source. Thus, the system comprises a catheter or endosocope comprising a light source at its proximal end, an optical probe at its distal end, and one or more light guides to transmit light from and to the proximal end and the distal end. The light emitter comprises an illumination light guide that transmits light from the light source to the distal end and the light collector comprises a collection light guide that transmits the emanating light from the distal end to the proximal end of the catheter. Briefly, the illumination light guide transmits light from the proximal end of the catheter to the distal end, where the light is launched onto the target tissue. The collection light guide collects light that emanates from the target tissue (such as reflected or fluorescent light) and transmits it to the proximal end of the catheter, where the light is made available for analysis.

The illumination light guide and the collection light guide can be a single light guide, which means that the same light guide can function as both the illumination light guide and the collection light guide. This is true for most aspects of the present invention. Alternatively, the illumination light guide and the collection light guide can be separate light guides.

In still yet another aspect that is similar to the aspect discussed in the preceding paragraphs, the present invention provides methods relating to the conduction of a biopsy that do not require that the distal tip of the catheter be adhered to the target tissue. Generally, the methods comprise the following steps. An optical probe is placed adjacent to a target tissue in vivo, which means sufficiently near or in physical contact with the target tissue such that light can be emitted to the target tissue and resultant emanating light can be collected from the target tissue (the light emitted by the target tissue can be fluorescence, reflectance or other light that is induced by the illumination light and directed toward the optical probe). Light is emitted from the optical probe to the target tissue under conditions suitable to cause light to emanate from the target tissue, to provide emanating light from an illumination area (which is the area illuminated by the light emitted by the optical probe). The emanating light striking the optical probe is collected and then evaluated to determine whether the target tissue comprises the one or more characteristics indicating that the target tissue should be biopsied, as discussed above.

If the target tissue comprises one or more characteristics indicating that the tissue may be unhealthy (i.e., in need of biopsy), additional methods further comprise obtaining the biopsy from the target tissue without removing the catheter from the body of the patient, and preferably without moving the distal end of the catheter within the patient. Keeping the distal end stationary between the optical scan and the biopsy facilitates obtaining the biopsy from the area of the target tissue that was illuminated by the optical scan, or the illumination area. Thus, these methods permit the same piece of tissue to be both scanned in vivo and biopsied. The methods may be implemented via the use of a catheter or endosocope comprising both an optical probe and a bioptome.

In yet a further aspect, the present invention provides methods for determining whether a target tissue comprises one or more characteristics indicating that a target tissue should be biopsied. Such characteristics are discussed above. The methods comprise placing an optical probe adjacent the target tissue. The optical probe comprises at least one light emitter and at least three light collectors that are equally radially distanced from at the least one light emitter, and light is emitted from the at least one light emitter to the target tissue under conditions suitable to cause light to emanate from the target tissue, thereby providing emanating light. Such emanating light that enters the at least three light collectors is collected, and the relative intensity of the collected light is measured for each of the at least three light collectors. This permits determination of the orientation of the optical probe with respect to the target tissue, which in turn provides information about the quality of the scan taken by the optical probe including whether some or all of the target tissue in the illumination area was too far from the optical probe to provide adequately significant data about such area.

Thus, the user can next determine whether the orientation of the optical probe relative to the target tissue is adequate to provide sufficient data about the one or more characteristics indicating that the target tissue be biopsied. The orientation of the optical probe to the target tissue is adequate to provide sufficient data about the target tissue when the optical probe is close enough and perpendicular enough to the tissue that the emanating light does not contain artifacts that interfere with the interpretation of the emanating light. The light emitted from the target tissue is strong enough to be collected by the optical probe and analyzed to provide meaningful information for the intended purpose, such as the determination of the presence or absence of characteristics of rejection. The optical probe has a suitable angle relative to the target tissue when the illumination light emitted by the probe strikes the target tissue generally evenly across the area of illumination such that the strength of the induced return light from the target tissue is representative of the state of the tissue across the area of illumination and collection. Preferably, the illumination light emitted from the optical probe is emitted perpendicular to the target tissue.

In view of the present specification, a person of ordinary skill in the art will be able to routinely select a set of data points that will fit a given situation. For example, such a person can select only data points above a certain intensity threshold, select only peak data points and/or select only data points that occur within a certain wavelength or range of wavelengths. Upon determining that the orientation is adequate, the light collected by each of the at least three collection light guides is then evaluated to decide whether the target tissue comprises the one or more characteristics indicating that the target tissue be biopsied.

As with the aspects of the invention described above concerning the determination of the orientation of an optical probe relative to a target tissue, the present invention also provides methods for determining one or more characteristics indicating that a target tissue should be biopsied wherein the methods comprise the use of at least three pairs of illumination light guides and collection light guides spaced as described above.

In the event that the target tissue is found to comprise characteristics indicating that a biopsy would be appropriate, then the methods optionally further comprise obtaining the biopsy, preferably of the same site that was optically scanned.

In this and other methods described herein, the methods are typically preferably performed on living animals, preferably human patients. Thus, the illumination light is transmitted and the fluorescence, or other return light, is collected in vivo.

In an embodiment that is preferred for in vivo optical scanning, particularly where the target tissue is a moving organ such as the heart, the timing of the illumination and collection (i.e., the optical scanning) is controlled and synchronized with movement of the organism and/or the target organ to enhance the utility of the information that is collected and processed. Briefly, as discussed above, measurements of target tissue are preferably made when the target tissue receives strong illumination and then emits strong fluorescence or other response (preferably a signal to noise ratio that is greater than about 5:1, further preferably greater than about 10:1) at a suitable orientation to be optimally collected and evaluated.

Figure 17:
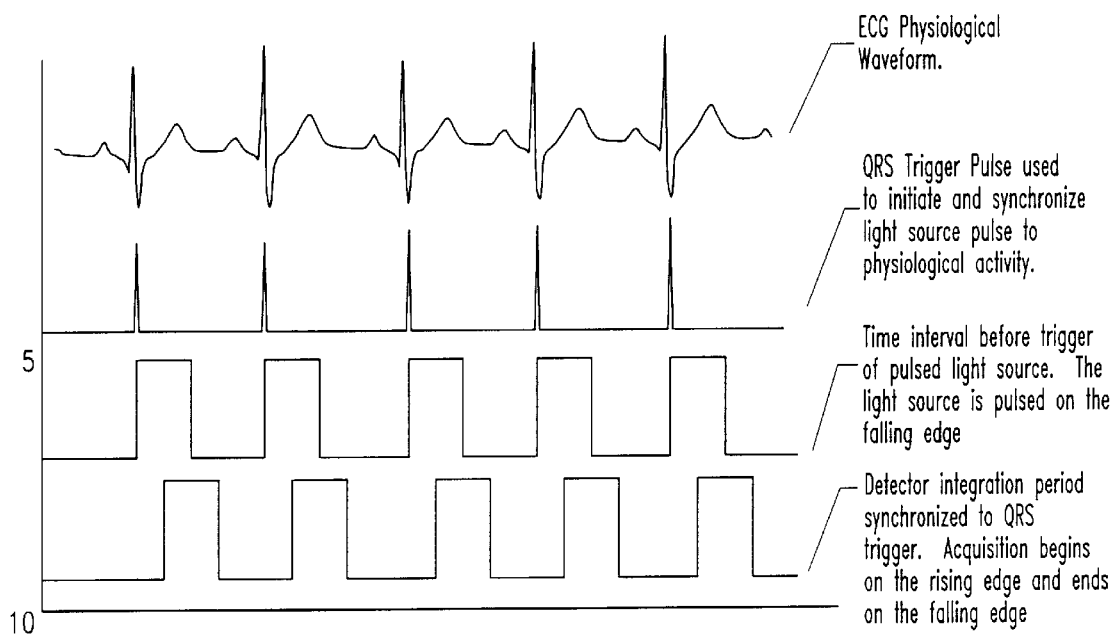
FIG. 17 is a graph of data acquisition triggered in accordance with an ECG.
Figure 18:
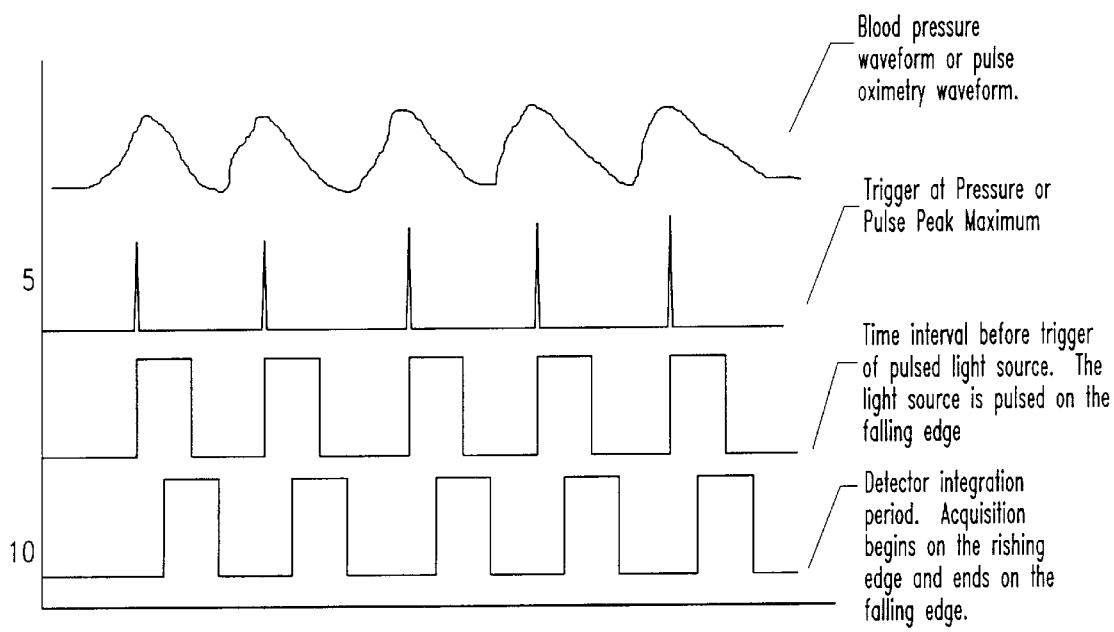
FIG. 18 is a graph of data acquisition triggered in accordance with a blood pressure monitor pulse oximeter.

Thus, in a preferred embodiment, the illumination and collection are both performed during a single diastole of a single heart beat (or other selected motion of the target tissue). This embodiment is particularly preferred when the target tissue is the heart. Determination of the diastole of the heart beat can be effected by a variety means that will be apparent to one of ordinary skill in the art in view of the present specification. For example, the user can detect an electrocardiogram of the heart beat of the host, and then use one or more signals, such as the QRS wave or other identifiable event, of the electrocardiogram to initiate or trigger the steps of transmitting and collecting during a single diastole of the heart beat. See, e.g., FIG. 17. Alternatively, the user can detect a pulse of the host using a blood pressure monitor, and then use the pulse to trigger the steps of transmitting and collecting. See, e.g., FIG. 18. In a preferred embodiment, a pulse oximeter, which measures the oxygen content of the blood, is used to provide the trigger that induces the scanning or date gathering.

In one preferred embodiment, the pulse is externally measured and the blood pressure monitor is located externally to the host, which means that the pulse is measured non-invasively. Typically, this means that the pulse measurement device does not traverse the skin or any membranes of the patient, although the device could be inserted into a body cavity; preferably, the measurement device does not enter the body, including body cavities. In another preferred embodiment, measurement of the pulse comprises using a pulse oximeter.

Figure 16:
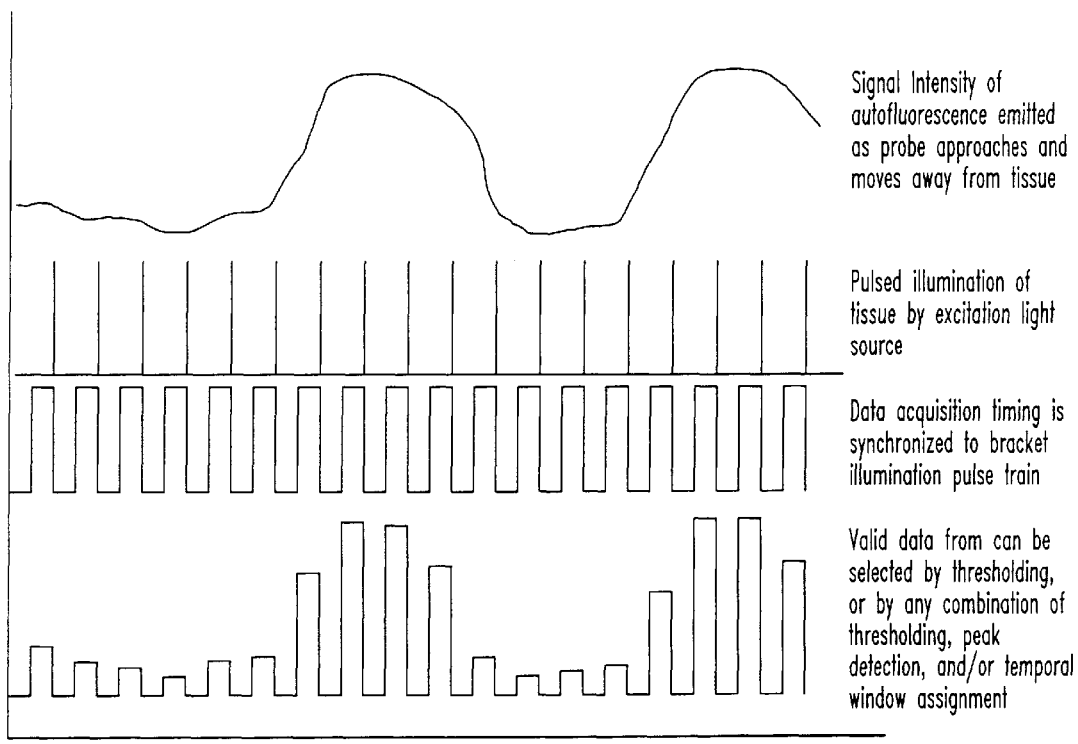
FIG. 16 is a graph of data acquisition pulsed a plurality of instances per heart beat.

In an alternative preferred embodiment, a plurality of measurements are obtained throughout the duration of the heart beat (or other motion). An example of this embodiment is depicted schematically in FIG. 16, which shows that the signal intensity of the fluorescence or emanating light varies as the probe approaches and moves away from the target tissue (such movement can also be caused by the target tissue approaching and moving away from the probe). When the tissue is then repeatedly induced to fluoresce or otherwise respond and the corresponding fluorescence or other response is synchronously collected, the information obtained provides a generally repetitive series of sequentially increasing and decreasing data points. The increases and decreases correspond to the movement of the heart during a beat, and therefore provide a measure of the heart beat. The data points can then be selected to provide optimal information about the target tissue, for example, by selecting only data points above a certain threshold, by selecting only peak data points and/or by selecting data points that only occur in a certain temporal locale within the beat. In addition, these data point selection criteria can be combined with physiological triggers such as an ECG or pulse measurement.

Absent such determination of proximity, orientation, and timing, the presence of motion, a poor angle of incidence of light, or too great a distance between the probe and the target tissue may produce artifacts such as a "smeared" measurement that does not represent a discrete site.

In a further aspect of the invention that relates to the other aspects discussed herein, the present invention provides methods similar to those described above comprising the use of Raman spectroscopy. Briefly, Raman spectroscopy detects the vibrational signatures of particular molecules inside a selected tissue, thereby providing chemical and other information about the tissue. Mahavedan-Jansen, A. and Richards-Kortum, R., *J Biomed. Optics* 1(1): 31–70, 1996; U.S. Pat. No. 5,261,410. At different rejection stages of a transplanted tissue (or other condition in other target tissue), the chemical compositions and the concentrations of certain molecules differ. Raman spectroscopy of the target tissue can be used to identify such condition. The wavelength bands used for determination of Raman spectra are molecule specific and provide direct information about the tissue comprising such molecules. A computer-implemented program makes use of the peak position(s), the relative intensities of different peaks to identify specific molecules and their relative concentrations relative to different tissue states.

In a preferred embodiment, the Raman spectroscopy is performed in vivo, further preferably through a catheter or endoscope as described herein. In one example of such a system, a fiber optic near infrared (NIR) Raman spectroscopy system is used. In particular, a near NIR diode laser (e.g., $\lambda$=785 nm, 830 nm) is used for the excitation illumination. At least one light guide, such as an optical fiber, conducts the illumination light through the catheter to the target tissue. At least one collection light guide then picks up the scattered light caused by the illumination light (which light includes Raman shifted photons) and then transmits the collected light to a spectrograph-CCD system for spectral analysis. Preferably, two filters are located at the tip of each of the illumination light guide and the collection light guide. A band pass filter is disposed at or near the distal tip of the illumination light guide, which filter eliminates the Raman signals generated by the illumination fiber and transmits only the excitation light to the target tissue. A long pass filter is disposed at or near the tip of the collection fiber, blocks elastically scattered laser light, and passes only the Raman shifted scattered light. In a preferred embodiment, the collected light is then transmitted to a high resolution grating which is used to disperse the Raman scattered light, and then a detector such as a back-thinned CCD array is used to acquire a spectral curve. A computer, preferably a PC computer, is then used for process control and spectral data analysis.

Characteristics of the lifetime decay of the autofluorescence of the transplanted tissue can also be used for the aspects of the invention discussed herein. The lifetime decay process of tissue autofluorescence depends on the types of fluorophore molecules present in the tissue and is very sensitive to the molecular environment of the fluorophores. At different rejection stages of the transplanted tissue, there are structural and chemical changes which lead to different fluorescence lifetime decay processes. The autofluorescence lifetime decay process follows multiple exponential functions, e.g., $I(t)=a_1\exp(-t/\tau_1)+a_2\exp(-t/\tau_2)$. In this example, each exponential term represents a different fluorophore type or different fluorescence emission process of a macromolecule. $\tau_1$ and $\tau_2$ are time constants that indicate the speed of decay and the ratio $a_1/a_2$ indicates the relative contributions of the two terms (fluorophores or fluorescence processes) to the fluorescence response. Such parameters ($\tau_1, \tau_2, \tau_1/\tau_2, a_1/a_2$) as well as their dependence on emission wavelengths can be used to differentiate different rejection stages.

Figure 23:
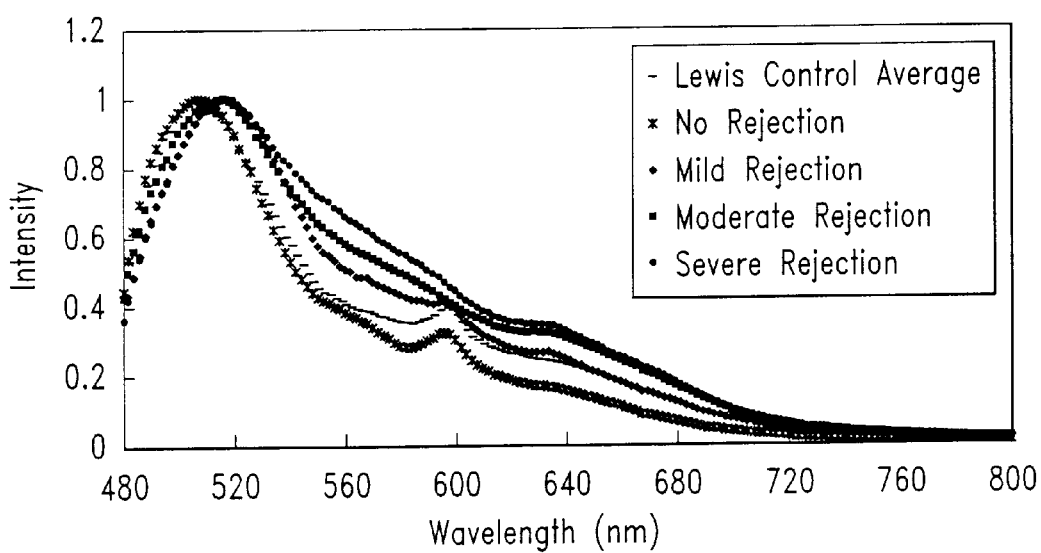
FIG. 23 depicts a block diagram of an exemplary system for fluorescence lifetime decay measurement.

FIG. 23 depicts a block diagram of an exemplary system for fluorescence lifetime decay measurement. A pulsed laser 140 generates laser pulses of picosecond or nanosecond pulse width. An illumination light guide 122 conducts the laser pulse to the target tissue site to excite autofluorescence. A collection light guide 120 collects the emitted autofluorescence signal and transmits it to a photon multiplier tube (PMT) 148 for detection. A lens 142 and/or band pass filter 144 are inserted in front of the PMT to select the desired emission wavelengths for analysis. The time gated photon count detection module 146 triggers the pulsed laser and captures the fluorescence lifetime decay process. A computer 10 is connected to the detection module to analyze the fluorescence decay process and calculate the decay parameters ($\tau$, a). In view of the present disclosure, algorithms can be developed and used by the computer to classify the tissue rejection stages according to the measured decay parameters ($\tau$, a). One advantage of the lifetime decay approach is that the time constant $\tau$ is an absolute value which is independent of the measurement geometry. Thus, involuntary movement of a target tissue or organ will have no effect on the measurement due to the measurement time scale of nanoseconds ($10^{-9}$ s).

In another alternative approach, the aspects of the invention discussed herein can be implemented based upon optical coherence tomography (OCT). Fercher, J. Biomed. Optics 1(2); 157–173 (1996). Implementation of OCT comprises the use of an interferometer such as an equal arm fiber optic Michelson-type interferometer. The interferometer comprises a light source wherein the light from the source is split such that one portion of the light travels along a reference arm (or control arm) and a second portion of the light travels along a sample arm, which arm is disposed within the catheter or endoscope body and ultimately transmits light to the target tissue. The light source emits a beam of pulsed continuous light. A portion of the light is transmitted along the sample arm to the target tissue, where it then enters the tissue (typically to a depth of 0–5 mm, usually from 0 or 1 mm–2 mm), while a mirror at the distal end of the reference arm can be axially displaced, thereby correlating to the depth in the tissue in which readings are taken. The light passes through the tissue and then is scattered or otherwise returned to the sample arm (please note, typically a single light guide provides both the illumination and collection functions in the sample arm). The resulting signals are then transmitted simultaneously back along the sample arm and the reference arm to a sensor; the optical interference between the two signals is measured by the sensor, then stored as an interferogram, which can be decoded to create a depth profile of the scattering characteristics of the tissue. The light exiting from the sample arm to the tissue is preferably collimated, for example via the use of a collimating lens at the distal end of the sample arm, and/or the light emanating from the sample arm can be scanned across the tissue (for example across about 2 mm of tissue) using either piezo or optical deflection techniques, to create a 2-D or 3-D profile of the tissue. Comparing such profile, or signature, of the target tissue to a known signature of the same type of tissue having a known status permits determination of the status of the target tissue.

In still another aspect, the methods of detection described above can be used to distinguish between different grades or level of rejection, for example by correlating the status of the transplanted tissue with the ISHLT or Billingham's levels described herein. Determination of the level of rejection can be determined, for instance by applying a linear discriminant function, then training the function to discriminate between the desired grades of rejection. For example, two groups of spectra are defined; a first group of spectra from a tissue known to have ISHLT grade 0, and a second group of spectra from the same type of tissue and known to exhibit ISHLT grade III rejection. Each spectrum comprises a set of features that comprise numeric information specific to that spectrum. In a preferred embodiment, the relative intensities at all wavelengths are evaluated to discriminate between the levels of rejection (the intensity of each wavelength being a separate feature), although the discrimination and training can also be performed on selected wavelengths. A computer-implemented program known as a stepwise feature selection algorithm is used to evaluate the wavelengths or features and then used to perform statistical calculations on various combinations of designated features to determine which combination(s) of features, when used in the linear discriminant function, is (are) capable of discriminating between the two groups of spectra. Preferably the program selects combinations that maximally discriminate between the two groups. This is referred to as "training" the discriminant function.

One example of such a linear discriminant function suitable for use as described is the following:

$$DF=a_0+a_1I(480)+a_2I(496)+a_3I(504)+a_4I(518)+a_5I(522) \quad a_0=-5.6;$$
$$a_1=-64.7; a_2=45.2; a_2=45.2; a_3=48.8; a_4=-115.5; a_5=64.1$$

In this function, I(480) means relative intensity at 480 μnm, I(496) means relative intensity at 496 nm, etc. The absolute value of the coefficients ($a_0$, $a_1$, $a_2$, ...) is dependent on the methods of normalizing the spectra. Selection of wavelengths and normalization of spectra will be apparent to a person of ordinary skill in the art in view of the present disclosure.

Once the linear discriminant function has been trained it can be used to score any spectrum, and can thereafter classify such spectrum into a desired category, such as ISHLT grade 0, I, II, III or IV. In addition, quadratic discriminant functions, neural network methods and other appropriate computer-implemented approaches can be used to discriminate between the grades of rejection.

Turning to apparatus provided by the present invention, catheter systems and catheters according to the present invention generally comprise an optical probe and/or other features. The catheter is typically applied to the subject by insertion into a vein in the neck or leg and subsequent guidance to the target tissue. For example, when the target tissue is the heart, the catheter is typically inserted percutaneously and then to and through the superior vena cava and into the right atrium and right ventricle of the heart. Also typically (approximately 80% of the time), the heart biopsy is taken from the apex end of the thick septum wall dividing the left and right ventricles in the heart. The catheters of the present invention permit optical scanning to be performed in areas where biopsy was not possible and also provide information regarding the status of the target tissue. Materials used in the construction of the catheters of the present invention, when intended for human use, should meet USP Class IV biocompatibility standards.

As a general discussion of catheter systems of the present invention, such systems comprise a catheter, as discussed above, that generally comprises a catheter body and a distal end designed for insertion into the patient, typically a human patient, a grip for physician control, and one or more light guides that can be connected to one or more light sources and one or more detectors. The light guides comprise one or more illumination light guides and one or more collection light guides. The illumination light guide can be the same light guide as the collection light guide, which means that in some embodiments the same light guide functions as both the illumination light guide and the collection light guide, and there need be only one light guide in the catheter.

The illumination light guide accepts light from one or more light sources and transmits it to its distal end, which is disposed within the distal end of the catheter. The light is emitted or launched, from the light guide into the tissue. The illumination light guide is preferably connected to the light source by an indexed mechanical coupling. The collection light guide collects light emitted by the target tissue and striking or entering its distal end, which is disposed within the distal end of the catheter. The collection light guide transmits the light from the tip of the catheter to one or more detectors. The light emitted by the target tissue can be any kind of light emitted by the target tissue, such as fluorescent light, which is typically induced by the illumination light, or reflectance light wherein illumination light is reflected from the target tissue. The collection light guide is preferably connected to the detector by an indexed mechanical coupling. The detector is typically located at the proximal end of the catheter. Examples of materials suitable for use as a light guide include optical fibers, fiber bundles or fiber arrays. In a preferred embodiment, the illumination light guide is optimized for blue or near ultraviolet light transmission, particularly where the illumination light induces fluorescence in the target tissue and the collected light is such fluorescence. The light guide collection is optimized for visible and near IR transmission.

Figure 14:
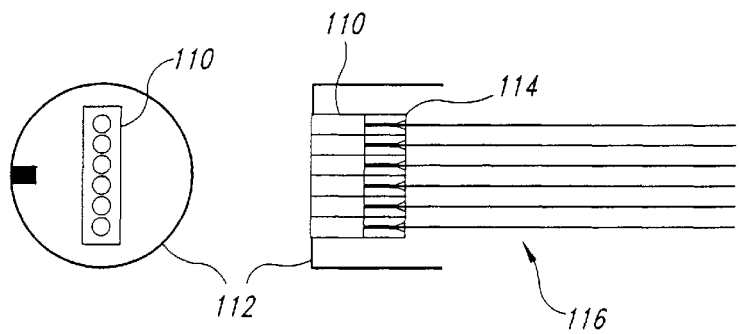
FIG. 14 is a schematic drawing of a proximal end termination of collection light guides to produce collimated output beam or beams.

At the proximal end of the catheter, the collection light guide, which transmits light to the detector, can be directed into a fitting that positions the fiber(s) of the collection light guide concentrically with a lens or lens array such as a gradient refractive index (GRIN) lens or lens array. The GRIN lens may be cut so that the one end of the lens is matched to the numerical aperture (NA) of the fiber and the opposite end is cut to emit a collimated beam of light. If more than one fiber is used, the GRIN lens array can be positioned as shown in FIG. 14 so that the beams can be projected in a line into a detector to facilitate wavelength separation and analysis.

The distal end of the catheter is generally designed to launch the illumination light to the target tissue and collect the light emanating from the target tissue.

Turning to specific aspects of certain apparatus of the present invention, one aspect provides an optical bioptome, which is an apparatus that combines an optical measurement device or probe with a tissue biopsy device or bioptome. As noted above, a bioptome is a device carried at the distal end of a catheter that snips off a piece of a target tissue for extraction from the organism and evaluation. Bioptomes often comprise a pair of opposing jaws, but other configurations are also known. U.S. Pat. No. 3,964,468; U.S. Pat. No. 54,953,559; U.S. Pat. No. 4,884,567; U.S. Pat. No. 5,287,857; U.S. Pat. No. 5,406,959; WO 96/35374; WO 96/35382; WO 96/29936; WO 96/35374. As one example, a bioptome can comprise a fluoro-polymer catheter type body bonded to a metal tip that incorporates mechanically actuated cutting jaws. The cutting jaws can be opened and closed by actuating a control in the hand piece of the catheter.

The device allows optical assessment of tissue to assist the surgeon in selecting sites and performing biopsy, and allows simple and easy biopsy with minimal risk and reduced harm to the patient because of shortened overall surgical procedure time and fewer insertions of catheters into the body.

The optical bioptome comprises a catheter or endoscope system comprising a light source that supplies light at a proximal end of a catheter, at least one illumination light guide suitable for conducting light from the proximal end to a distal end of the catheter and for emitting the light from a distal end of the illumination light guide, at least one collection light guide suitable for collecting light entering the distal end of the collection light guide and conducting the light to the proximal end of the catheter, and a bioptome. In a preferred embodiment, the illumination light guide and the collection light guide are the same optic fiber.

The catheter comprising the optical probe and a bioptome can be designed in a variety of configurations. For example, the catheter can be prepared so that when the jaws of the bioptome are opened the optical probe is extended past the open jaws to the target tissue, where the optical probe can then make a measurement. When the jaws are released (i.e., closed) the optical probe is retracted into its lumen within the catheter exterior. The bioptome and the optical probe can also be disposed side-by-side or concentrically within the catheter. Thus, the bioptome and the optical probe can be disposed equally extended with regard to the distal tip of the catheter, one can be disposed more extended than the other, or one or both can be extendible and retractable according to the needs of the user.

The optical probe and the bioptome can be modular or they can be integrated in a single assembly. As with other catheters and devices described herein, each of the optical probe and the bioptome can be sterilized or destroyed after use.

In a further aspect, the present invention provides a catheter system suitable for emitting and collecting light, the catheter system comprising a light source that supplies light at a proximal end of a catheter, at least one illumination light guide suitable for conducting light from the proximal end to a distal end of the catheter and for emitting the light from a distal end of the at least one illumination light guide, and at least three collection light guides, each collection light guide suitable for collecting light entering the distal end of the collection light guide and conducting the light to the proximal end of the catheter, wherein the collection light guides are equally radially disposed around the at least one illumination light guide. As with many other aspects of this invention, the light guide ends are preferably flat cut and polished flush with the distal tip of the catheter.

In a functionally related aspect, the present invention provides a catheter system suitable for emitting and collecting light, the catheter system comprising a light source that supplies light at a proximal end of a catheter, at least three pairs of light guides, each pair comprising an illumination light guide suitable for conducting light from the proximal end to a distal end of the catheter and for emitting the light from a distal end of the illumination light guide and a collection light guide suitable for collecting light entering the distal end of the collection light guide and conducting the light to the proximal end of the catheter, and wherein the distance from the collection light guide to the illumination light guide is equal in the at least three pairs.

These aspects of the invention are functionally related because they can be used to determine if the distal end is perpendicular to the target tissue and/or in contact with or near to the target tissue. The spacing between the light guides and the diameter of the light guides, which can be routinely selected by a person of ordinary skill in the art in light of the present disclosure, determine the depth layer of the target tissue from which optical property information is collected. As discussed above, independent measurement of the signal intensity from each collection light guide permits elucidation of the orientation of the distal tip and the target tissue, which can be used to indicate the quality of the measurement. Thus, in sum, these aspects are preferred when the user desires to determine the orientation of the distal end (and the optical probe carried therein) relative to the target tissue and/or to selectively collect light from a certain desired depth of the target tissue.

In still a further aspect, the present invention provides a catheter system suitable for emitting and collecting light, the catheter comprising at least one light source that supplies light at a proximal end of the catheter and a plurality of light guides, wherein at least two of the light guides are suitable for conducting light longitudinally along the catheter, and for emitting and detecting light at different sites located along a distal end of the catheter, such that the catheter is capable of emitting and collecting light at a number of different sites along the distal end of the catheter without moving the distal end. See FIGS. 19a–d.

Figure 19A:
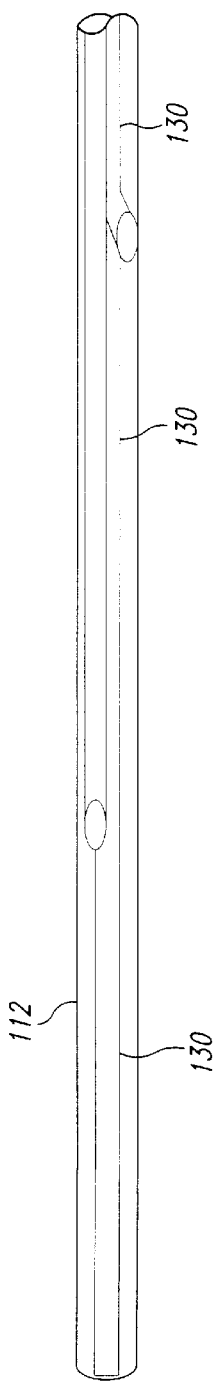
FIGS. 19a–d depicts views of a catheter comprising a plurality of light guides and optical ports.
Figure 19B:
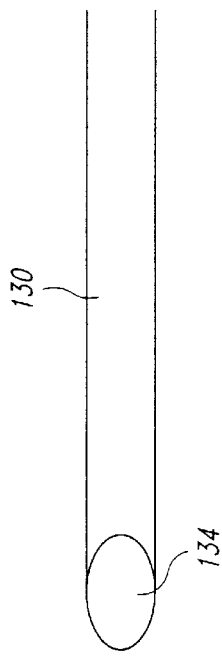
Figure 19C:
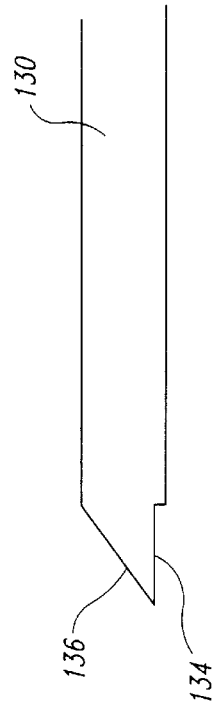
Figure 19D:
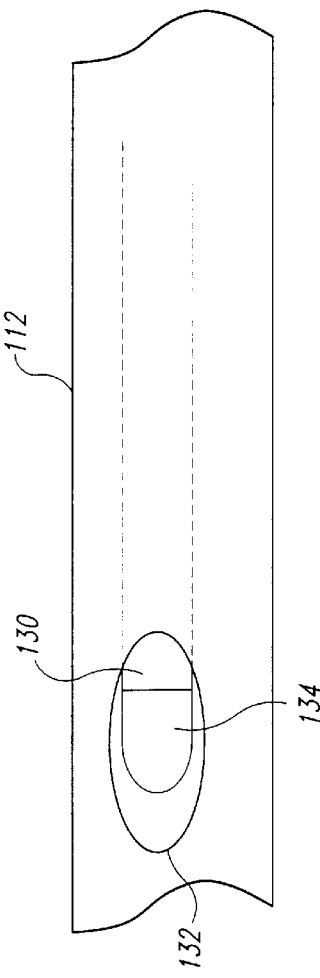

Thus, the catheter comprises a plurality, preferably three or more and further preferably six, optical ports 132 along the distal end of the catheter. Preferably, the ports form a spiral along the side of the distal end of the catheter, although the ports can also be in a line or otherwise spaced along the distal end of the catheter. One or more of the optical ports can also be located at the distal tip of the catheter. The optical ports typically provide a view or scan that is perpendicular to the axis of the catheter, although the optical ports can be either forward-looking or rear-looking if desired. Each of the optical ports provides a window for at least one illumination light guide and at least one collection light guide. The same light guide 130 can function as both the illumination light guide and the collection light guide, or the illumination and collection light guides can be provided in pairs (or in other combinations according to the needs of the user). Each of the pair of light guides is preferably positioned such that the light launched from the illumination light guide and the light collected by the collection light guide focus on the same location in the target tissue. In one embodiment, as depicted in FIGS. 19b–19d, the light guides 130 have a 45° angle 136 at their distal ends to provide a reflective flat surface 134 that emits and collects light in a side-viewing fashion.

The 45 degree surface at the distal end of the light guide is one preferred embodiment because it facilitates perpendicular viewing from the side of the catheter. The distal ends of the light guides are then positioned to transmit illumination light through the optical ports and to the target tissue, and to receive light from the target tissue through the window. Preferably, the distal ends of the light guides are contacted with the optical ports and are immobile with respect to such optical ports, preferably via use of an optically clear non-fluorescent epoxy. The 45 degree surface of the light guides can be coated with a reflective, non-fluorescent coating.

Each of the light guides (or pairs of light guides) can be placed in a lumen maintained within the catheter, to give a plurality of lumens spaced equally around the inside of the catheter. In one embodiment, each lumen ends at a different distance to provide the light guide(s) therein access to the appropriate optical port in the distal end of the catheter. In another embodiment, each of the lumens is the same length, and optical ports are cut into the outer side of each of the lumens at various distances from the distal tip of the catheter.

The resultant catheter has a plurality of optical ports that spiral up the side of the catheter from the distal tip and can be used to make measurements of the target tissue at various distances from the apex by rotating the catheter so that the port is in contact with the tissue.

In still another aspect of the invention, the light guides (again preferably flat cut and polished) are recessed from the distal tip of the catheter rather than flush with it. Co-luminal with the fibers is a liquid-carrying lumen that allows a bolus of non-fluorescing, non-reflecting liquid saline solution to be pumped to the distal tip of the catheter. The structure of the catheter tip directs the liquid around the optical fibers and out to the tissue so that the resultant jet of liquid pushes aside blood or other interfering material and acts as a liquid light path for transmission of light to, and collection of light from, the target tissue.

In still a further aspect of the invention that is somewhat similar to that discussed in the preceding paragraph, the distal tip of the catheter is covered with and bonded to an elastomeric balloon comprising an optically transmissive window that is preferably non-fluorescing and nonreflective. Upon insertion of the catheter into the right ventricle, a bolus of gas or liquid is pumped into the balloon to cause it to distend and thereby contact the window with the tissue. The liquid or gas, which can be air, in the balloon acts as an optically clear path to the tissue, while the balloon pushes blood and other interfering material out of the field of view.

Figure 9:
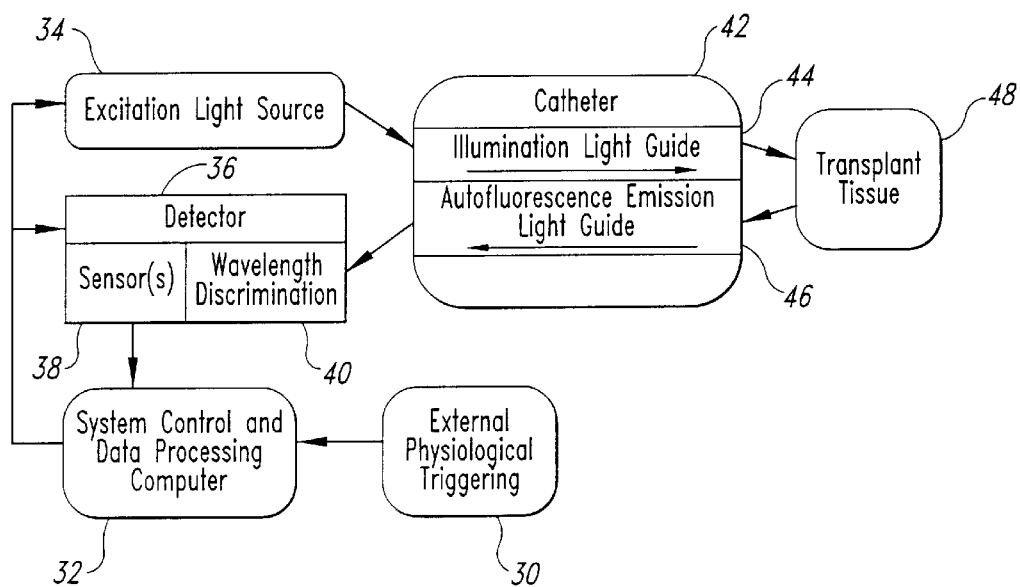
FIG. 9 is block diagram of a computer controlled catheter system suitable for use with the present invention.

In a preferred embodiment, the methods and catheter systems and other apparatus described herein are operably linked to a computer containing at least one computer implemented program that implements at least one facet of the methods, catheter system and/or other apparatus. In a preferred embodiment, the program is able to determine the spectrum of light collected by the collection light guide, determine an intensity of light collected by the collection light guide, compare the relative intensity of light collected by a plurality of collection light guides and/or time when light is to be transmitted along the light guides in concert with a pulse or electrocardiogram. An example of a system is depicted in FIG. 9. In FIG. 9, an external physiological trigger 30 is received by system control and data processing computer 32, which in turn is linked to excitation light source 34 and transmits light via illumination light guide 44 (contained within catheter 42) to transplanted tissue 48. The autofluorescence emission or other response is collected and transmitted via collection light guide 46 and to detector 36, where sensors 38 and wavelength discriminator 40 are located, which system then signals the system control and data processing computer 32.

Generally speaking, a computer suitable for use with the various aspects of the present invention comprises a user interface, a system control, and devices for data acquisition, processing and management. Briefly, the user interface typically comprises devices such as probes, keyboards and screens for the entry and display of patient data and session information, system parameters and current control parameters and data collected. The system control typically effects system timing, light source pulsing and data acquisition timing. Data acquisition typically concerns synchronization with physiological signals, signal conditioning and preprocessing, and data acquisition and storage. Data Processing typically concerns data quality verification, data signal processing and data analysis. Data management typically concerns a structured data storage, data integrity check, data security, data backup and data reporting. Certain preferred embodiments suitable for use for these aspects of the present invention are discussed in U.S. patent application Ser. No. , filed Mar. , 1998 and entitled Validating and Processing Fluorescence Spectral Data for Detecting Rejection of Transplanted Tissue.

The following discussion sets forth some of the components that are advantageous for use with the methods and apparatus of the present invention. Briefly, systems suitable for implementation of optical scanning such as is described herein generally comprise a light source to generate appropriate excitation wavelength(s), a detector that selects and measures the appropriate wavelengths of the fluorescence emitted, and, preferably, a data processing and control system with software that controls the timing of illumination and detection and processes the acquired data.

Light Sources

The present invention can use any light source that provides a light that induces fluorescence in the target tissue. For some aspects of the invention, the light source need not induce fluorescence, but may instead cause reflectance or other light to be emitted from the target tissue. Selection of an appropriate light source is well within the ordinary skill in the art in view of the present specification. With regard to light sources that induce fluorescence, the light source can be selected to provide light from ultraviolet (UV) through visible light. Preferably, the light comprises blue or near-UV light. Also preferably, and particularly for in vivo aspects of the invention, the light does not comprise UV light because such light can induce cancer or other problems within the patient organism, which is preferably a human being. Further preferably, the light consists essentially of blue light and/or green light.

Figure 11:
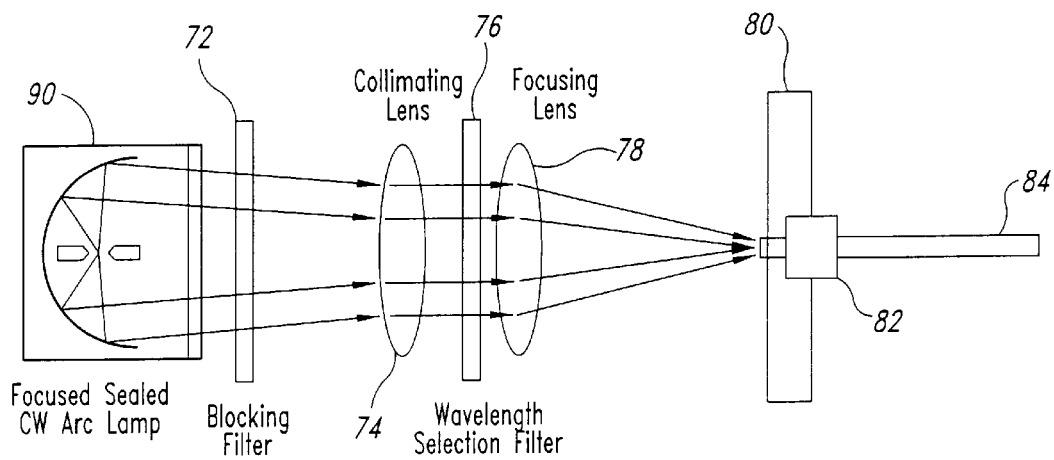
FIG. 11 is a schematic drawing of a focused continuous wave (CW) arc lamp.
Figure 12:
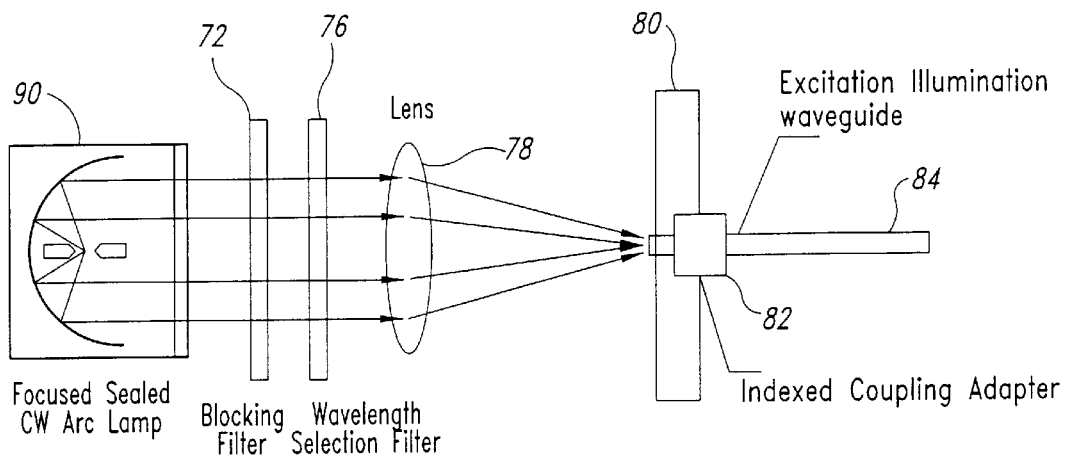
FIG. 12 is a schematic drawing of a collimated CW arc lamp.

Some examples of preferred light sources to generate the required excitation energy include a pulsed xenon flashlamp equipped with wavelength selection filters (FIG. 10), a CW (continuous wave) mercury or xenon arc lamp equipped with wavelength selection filters (FIGS. 11 and 12), a Blue or UV CW laser, and a Blue or UV pulsed laser. These are discussed below. The light sources in these figures preferably have an indexed mechanical coupling adapter 82 maintained in a base 80 to ensure that the illumination waveguide 84 is positioned to maximize the light entering the fiber, and are preferably controlled by system software, which controls pulse timing of the arc lamp power supply.

Figure 10:
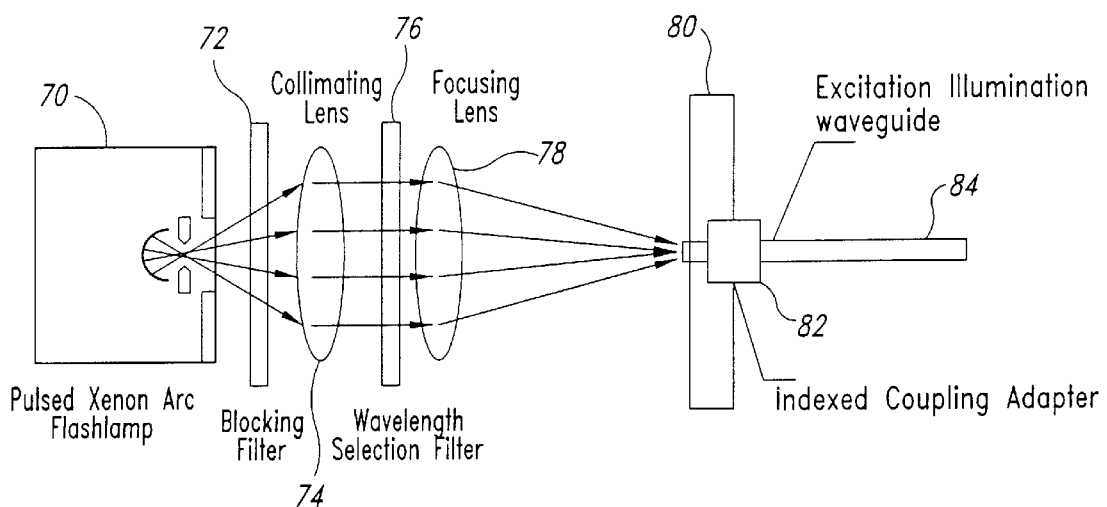
FIG. 10 is a schematic drawing of a pulsed xenon flashlamp source.

In FIG. 10, a pulsed xenon flashlamp 70 comprises a sealed housing arc lamp and power supply. The arc lamp typically has an arc length of less than 2 mm and is optionally equipped with an integral reflector to maximize energy directed toward the illumination light guide of the catheter or optical probe. An optical filter or series of filters such as a blocking filter 72 and wavelength selection filter 76 placed in the optical path can select the wavelength of the illumination light. The energy emitted by the arc lamp is collected and focused by a focusing lens 78. A collimating lens 74 can be placed between the filters if desired. In a preferred embodiment suitable for use with the present invention, the lenses are selected to direct the energy in a converging cone into an illumination light guide, with an apex angle that is less than or equal to the acceptance angle of the illumination light guide as defined by the numerical aperture of the illumination light guide.

A CW mercury or xenon arc lamp light source (FIGS. 11 and 12) comprises a sealed housing arc lamp 90 and power supply. The arc lamp typically has an arc length of less than 2 mm and is optionally equipped with an integral or external reflector to maximize energy directed toward the illumination waveguide of the catheter or optical probe. An optical filter or series of filters placed in the optical path can select the wavelength of the illumination light. The energy emitted by the arc lamp is collected and focused by a lens system. The lenses are selected to direct the energy into the illumination light guide in a converging cone with an apex angle that is less than or equal to the acceptance angle defined by the numerical aperture of the illumination light guide. In one embodiment, the lamp power supply operates continuously with no pulsing. Alternatively, the lamp can be powered by a sinusoidally varying current/voltage, which can also enhance the blue wavelength emission of the lamp.

A blue or UV CW laser light source comprises a laser that emits light in the blue or near ultraviolet wavelengths. Wavelength selection can be accomplished by using a laser such as a Helium-Cadmium (HeCd) laser or a Krypton-Argon laser that emits in the blue portion of the spectrum. Alternatively, a dye laser pumped by a shorter wavelength laser wherein wavelength selection is a function of dye characteristics and cavity monochrometer tuning can be used. The energy emitted by the laser is collected and focused by a lens system. The lenses are selected to direct the energy into the illumination light guide in a converging cone with an apex angle that is less than or equal to the acceptance angle defined by the numerical aperture of the illumination light guide. The laser can be equipped with a manual and/or computer controlled shutter.

A blue or UV pulsed laser light source comprises a laser that emits light in the blue or near ultraviolet wavelengths. The laser emits short duration pulses, preferably under software program control. Wavelength selection can be accomplished by using a dye laser pumped by a shorter wavelength laser wherein wavelength selection is a function of dye characteristics and cavity monochrometer tuning. Alternatively, a longer wavelength laser equipped with a frequency doubling system and/or an optical parametric oscillator (OPO) can be used. The energy emitted by the laser is collected and focused by a lens system. The lenses are selected to direct the energy into the illumination light guide in a converging cone with an apex angle that is less than or equal to the acceptance angle defined by the numerical aperture of the illumination light guide.

Detectors

Detectors suitable for use with the present invention separate the fluorescence light emitted by the target tissue, and typically conducted to the detector from the target tissue by a collection light guide, into wavelength regions of interest and produces a signal proportional to the fluorescence emission of each of the regions of interest. The present invention can use more than one detector if desired. The detector is typically controlled by the system software so that start of acquisition and integration time can be synchronized with the shuttering and pulsing of the illumination system and with the physiological triggers. Exemplary detectors include a charge coupled device (CCD), charge injection device (CID), intensified CCD detector, photomultiplier tube (PMT) detector array, photo-diode array (PDA), intensified PDA and an avalanche photo-diode (APD) array.

The fluorescence light collected by the collection light guide can be directed to a wavelength dispersive grating or prism and the resultant spectrally distributed light is projected onto the selected detector array(s), which has been calibrated for wavelength and intensity. The resulting signal then typically undergoes signal processing and discriminant analysis by the system software to determine whether the signal comprises the optical characteristics of tissue undergoing rejection.

In a preferred embodiment, the fluorescence is collected by multiple collection light guides and is projected onto the selected detector array such that the signal for each collection light guide can be analyzed independently. This type of multiple collection light guide/2-D detector array (which can also be implemented with other types of detector arrays) can be particularly helpful for analysis of information to elucidate probe orientation, distance and mobility relative to the target tissue.

In another preferred embodiment, the fluorescence light from the target tissue is directed into an optical beam splitter that divides the light into two or more spectral regions of interest. The spectrally separated components are then each directed to discrete detectors. In preferred embodiments, detectors can be silicon detectors, photomultiplier tubes or avalanche photo diodes, although other detectors can also be used advantageously with this embodiment of the invention.

The System Controller Program

The system controller program controls the timing of the emission of the light that induces emanation of light from target tissue, typically by controlling the pulsing or shuttering of the light source. It also controls and synchronizes the timing of emanation light acquisition and detector integration with the operation of the light source, and in a preferred embodiment controls and synchronizes the timing of such light actions with external or internal physiological measurement triggers, such as an electrocardiogram (ECG) or the pulse generated by the heart beat. In one preferred embodiment, the measurement of the pulse comprises the use of a pulse oximeter. In the ECG triggering mode, the software synchronizes illumination and collection windows with specific signals, or waves, within the ECG, such as the QRS wave. One advantage of an ECG trigger is that the ECG can be obtained from an external patient electrocardiograph monitoring device or system. Pulse oximeter triggering mode permits the user to trigger timing of various actions from an external pulse oximeter monitoring device or system.

Using the system controller program, the user can set a time interval for desired events. For example, the user can set a time interval after the physiological trigger or after initiation of data acquisition when the light source will be pulsed or shuttered, when data acquisition will begin, and/or when data will be measured, integrated and/or analyzed. See FIGS. 17 and 18. Alternatively, such interval(s) can be set automatically by the system controller program.

In an alternative preferred embodiment, which can be considered an internal optical triggering mode, the system continuously triggers the light source and/or detector at a set frequency to provide a plurality of measurements over the duration of a single heart beat. See FIG. 16. As the optical probe comes in proximity with the tissue the light signal collected by the probe increases. The software can monitor the signal for a local temporal intensity maximum in illumination or emission of the target tissue, and then select a window of desired data at a selected time at or near the time of the trigger, which can before, during and/or after the trigger. As an alternative to, or in conjunction with, the temporal window, an intensity threshold window can be defined for desired data.

Physiological triggering such as ECG or pulse monitoring can be used in conjunction with the threshold window, the temporal window and/or other data selection methods described above.

After data acquisition, in one embodiment, the system controller program can process the data to determine the relative responses of the intensity of the spectral regions of interest. This information can then be compared to the responses characteristic of normal and abnormal tissue and then shown by a display, such as a numerical or graphic display, to assist the surgeon in evaluating the tissue and/or determining appropriate sites for biopsy.

The following Examples are offered by way of illustration, and not by way of limitation.

EXAMPLES

Example 1

Rat Heart Transplant Model

A. Abdominal allograft and isograft rat heart transplant models were used to evaluate tissue rejection by detection of fluorescence. The models allow for the transplant recipient rat's heart as an internal control. Allografts (different rat strains) and isografts (same rat strains) were treated with cyclosporin or untreated. The protocol for this Example was depicted schematically in FIG. 1.

Turning to the experiment itself, a 250–350 g F344 rat was anaesthetized and, using a surgical microscope, a ziphopubic incision was made to free the abdominal aorta and inferior vena cava below the origin of the renal vessels. A donor rat (150–200 g Lewis rat) was then anaesthetized and the heart was isolated. Ties were placed around the inferior and superior venae cavae and the pulmonary artery and thoracic aorta were transected 3 to 5 mm distal to their origins. A ligature was placed around the pulmonary veins. The heart was removed from the thoracic cavity and placed in saline. A donor heart was placed in the abdominal cavity of the F344 recipient, and microvascular anastomoses were completed between the recipient inferior vena cava and donor pulmonary artery and the recipient abdominal aorta and donor thoracic aorta. Syngeneic grafts (Lewis-to-Lewis and F344–to–F344) were performed in the same manner.

Figure 2:
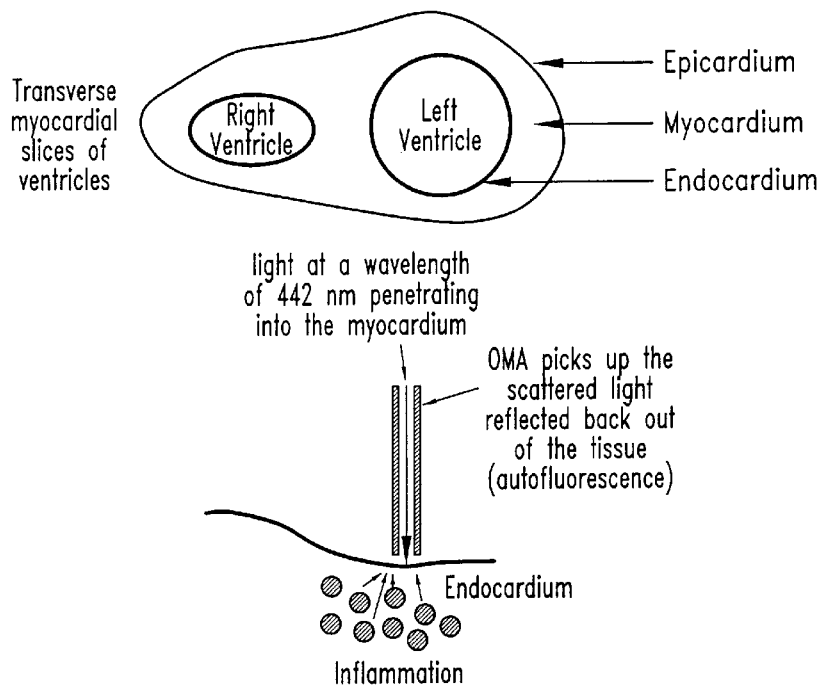
FIG. 2 is a schematic diagram of the heart and of a light pathway in heart tissue.

On the day of sacrifice, the transplant and the host heart were taken from each rat. The atria were frozen and the ventricles were cut into 3 transverse cross sections. The posterior walls were opened and spectral measurements were acquired, as depicted in FIG. 2. Following the spectral measurements, the ventricular sections were fixed either in 10% buffered formalin for histo-morphological studies including histological evaluation, tests for cell death, and assays to evaluate protein and gene expression, or frozen in OCT for archive.

FIG. 2 was a schematic diagram of the light pathway and heart tissue indicating the section or slice of the ventricle that was taken and a method of achieving the spectral measurements.

B. Fluorescence spectroscopy.

Figure 3:
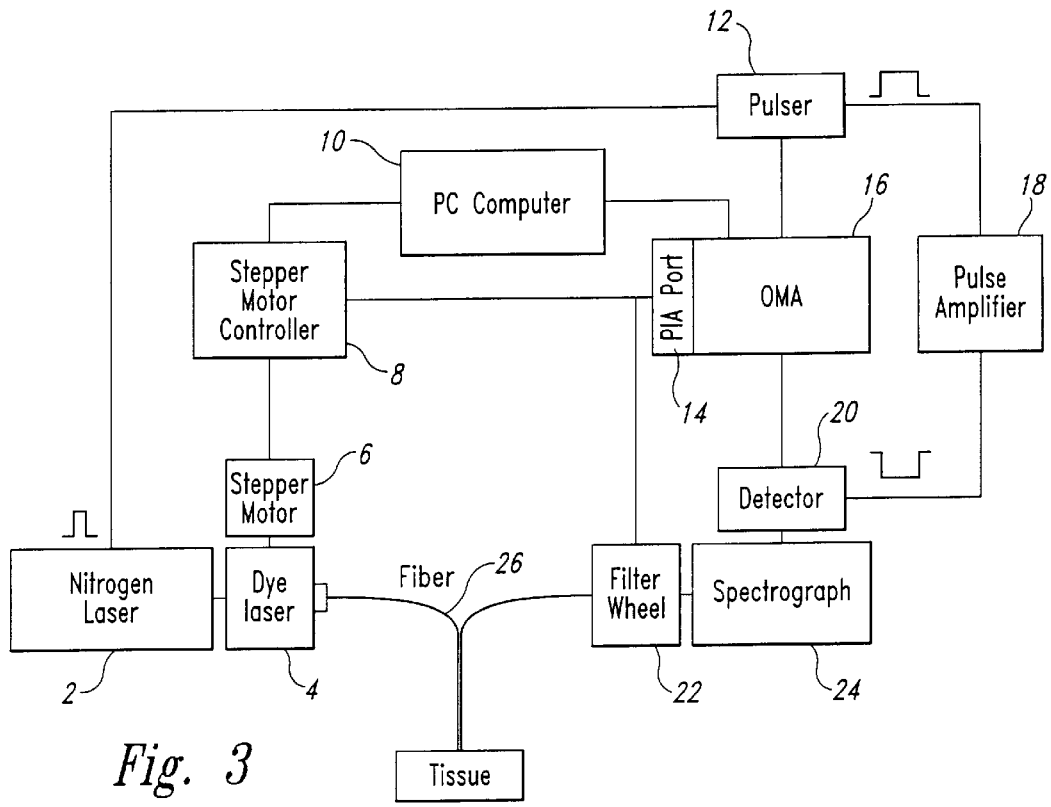
FIG. 3 is a block diagram of a Nitrogen Dye Laser-CCD spectrometer system suitable for measurement of in vivo tissue fluorescence spectra under multiple wavelength excitation.

The system to measure spectroscopy, illustrated in block diagram form in FIG. 3, comprised a Nitrogen Dye Laser 2, 4 with stepper motor 6 and stepper motor controller 8 for wavelength selection, an optical multi-channel analyzer (OMA) 16 with gated intensified detector, and a PC computer 10 (other computers could also be used). A bifurcated fiber optic bundle 26 was used to conduct the excitation or illumination laser light and to collect and return the fluorescence light to the detector 20. Gating electronics (pulser 12 and pulse amplifier 18) were used to achieve a high signal to noise ratio, allowing fluorescence measurements to be performed with ambient light on. Excitation wavelength changes were performed automatically and quickly by the stepper motor 6 which was controlled by the OMA PIA (peripheral interface adapter) port 14 using the OMA data acquisition (DAD) program. The filter wheel 22 in front of the spectrometer 24 was also controlled by the PIA port to change the barrier filters when different excitation wavelengths were used.

Figure 4:
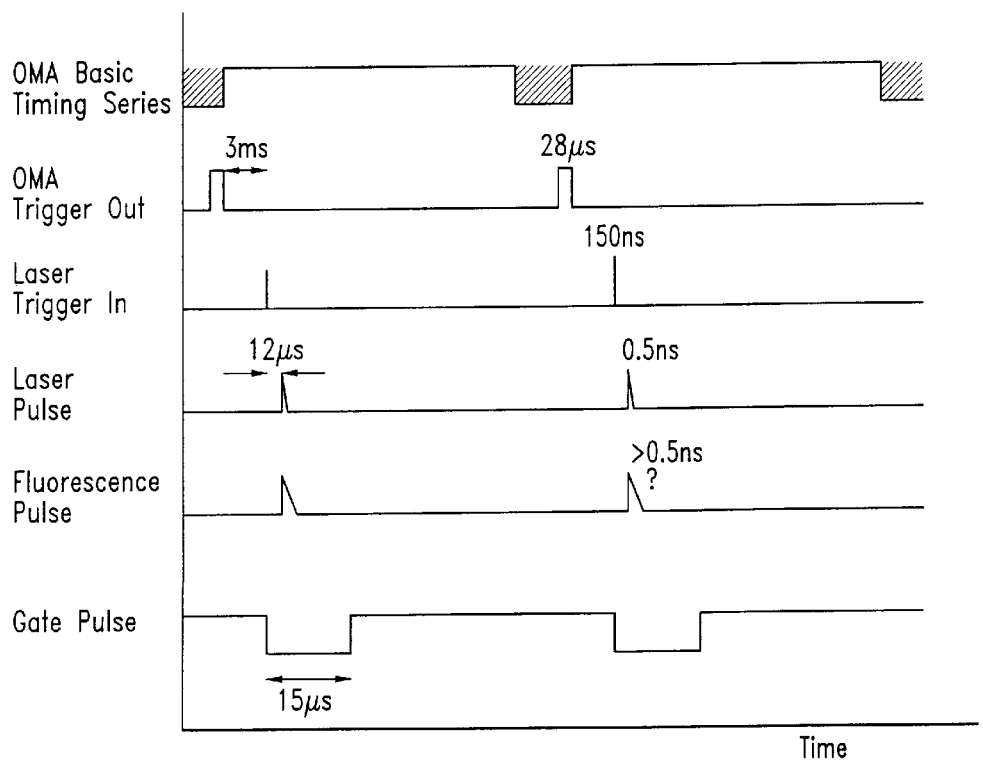
FIG. 4 depicts the timing sequence for operation of the a nitrogen Dye laser-CCD spectrometer system.
Figure 5A:
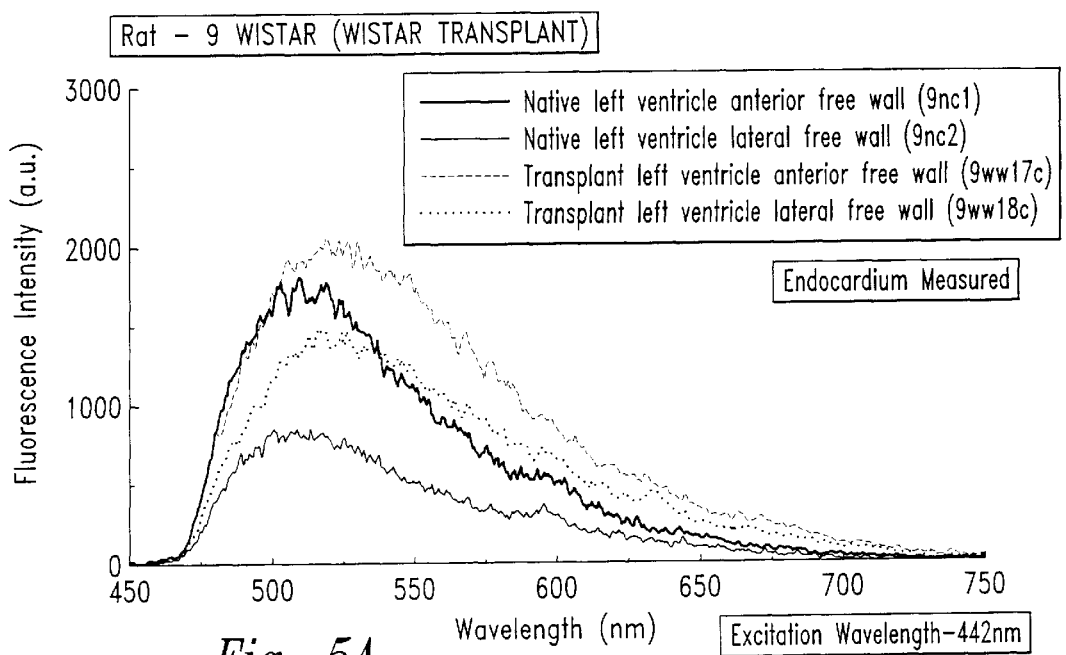
FIGS. 5a through 7b depict fluorescence spectra.
Figure 5B:
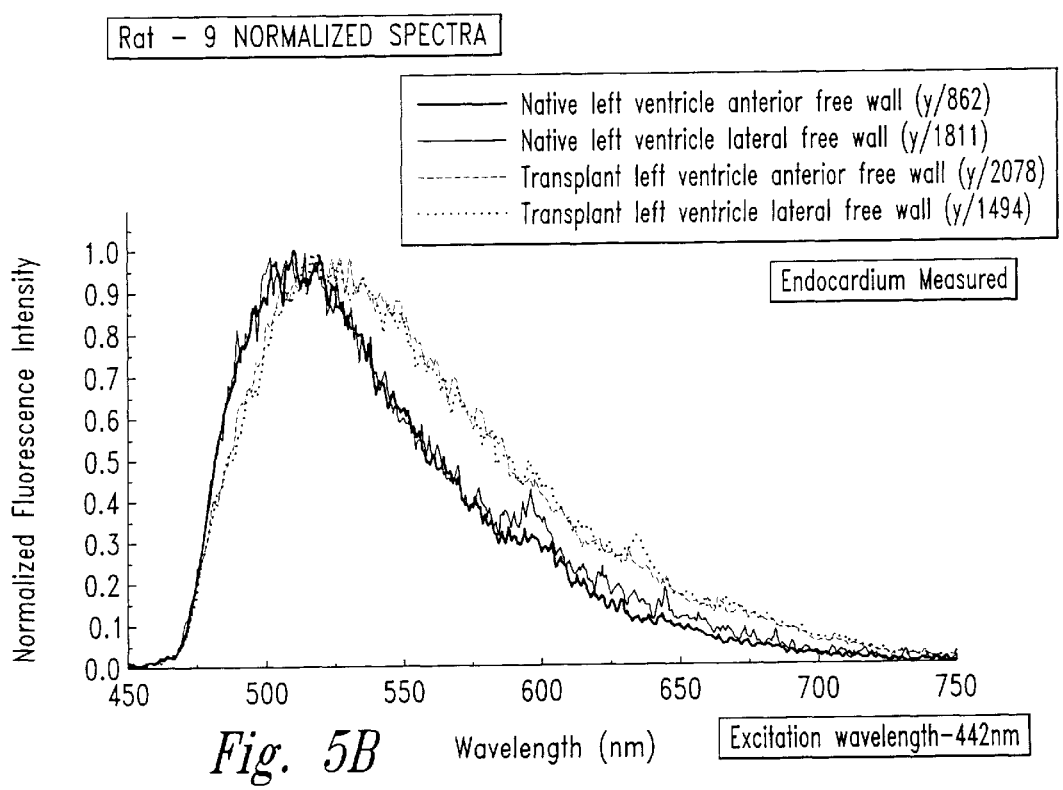
Figure 6A:
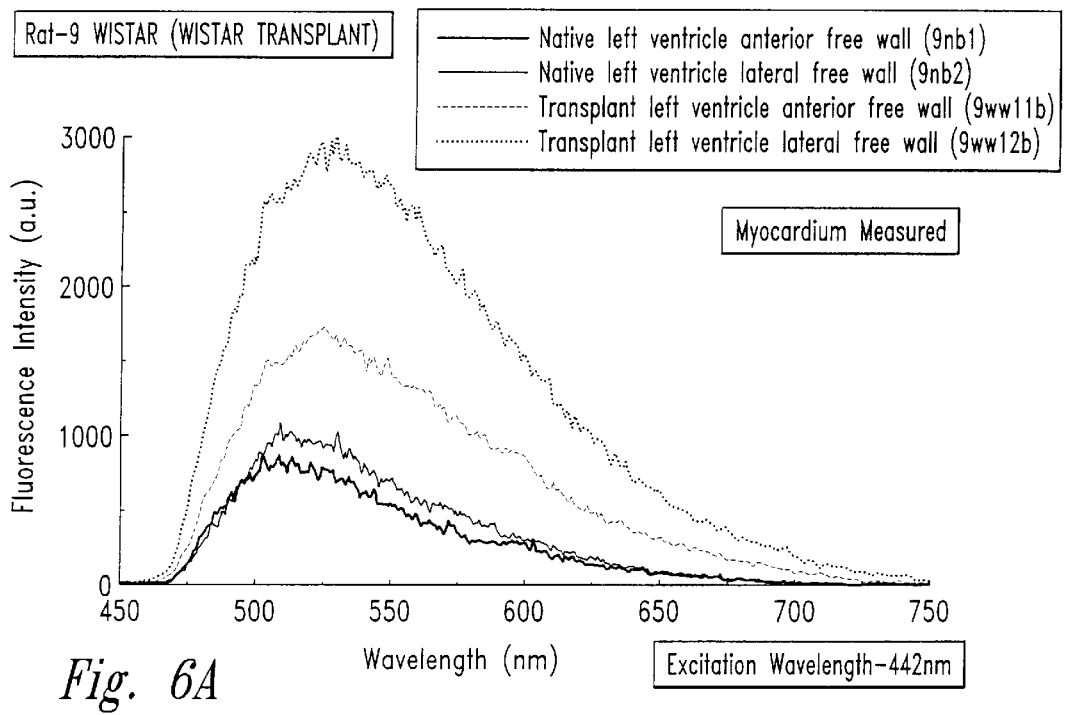
Figure 6B:
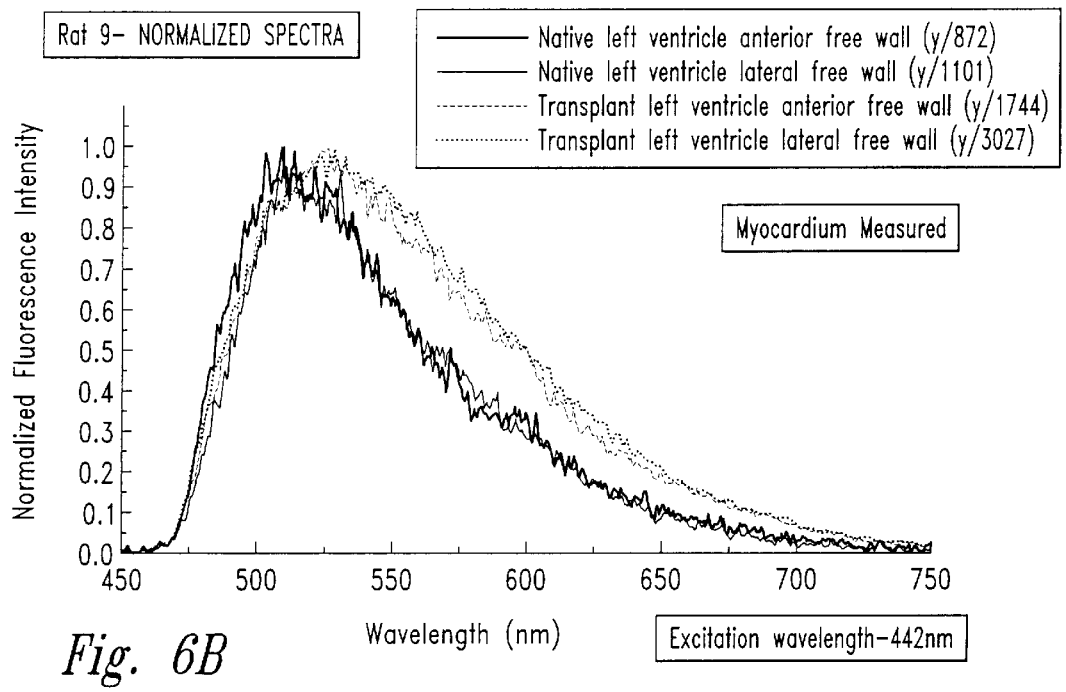

Operation of the system was illustrated in FIG. 4, which was a timing sequence for operation of the Nitrogen Dye Laser-OMA system. The DAD program directs the OMA to send a 28 µs pulse to the pulser. Three milliseconds later, the pulser triggers the pulse amplifier and the laser. Twelve microseconds after being triggered the laser emits a 0.5 ns wide laser pulse. The high voltage negative gating pulse was kept active for 15 µs after the laser trigger pulse was fired to make sure all the fluorescence photons were collected. The gating pulse width is still much shorter than the basic OMA exposure time (=30 ms). Therefore, a high signal to noise ratio was achieved. When the spectral measurement at one excitation wavelength was completed, the stepper motor controller was triggered to change the wavelength. When the wavelength change was complete, the stepper motor controller signals the OMA that spectral data acquisition can begin again. With the same laser dye, the wavelength change takes less than one second.

Figure 7A:
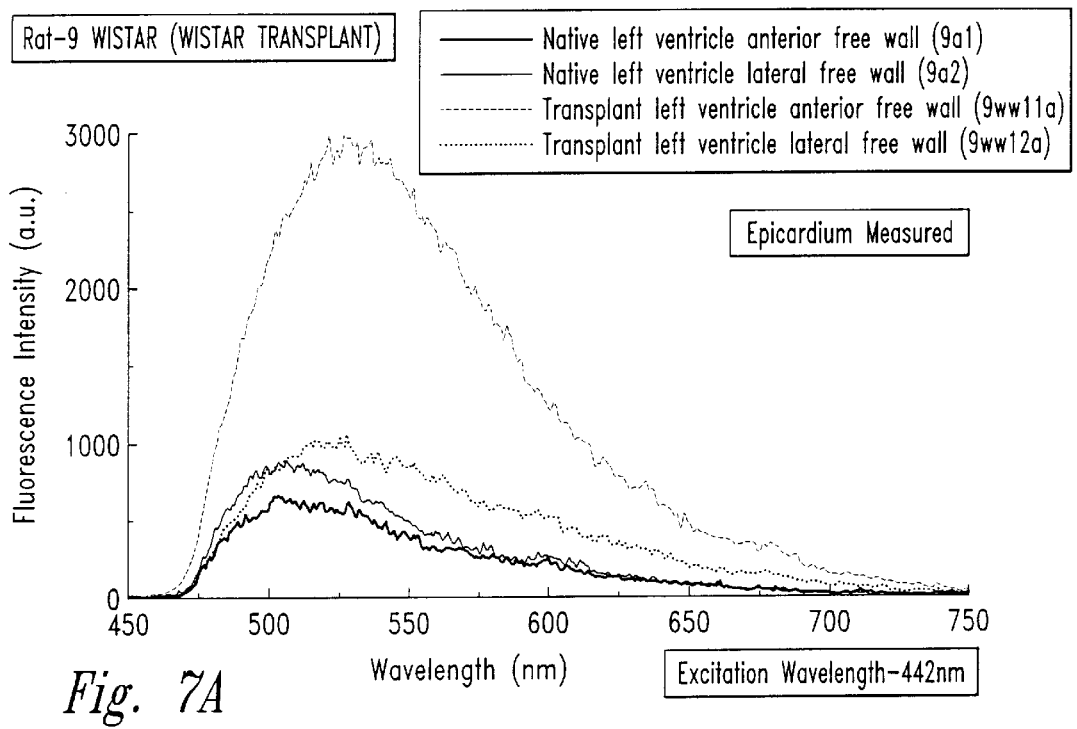
Figure 7B:
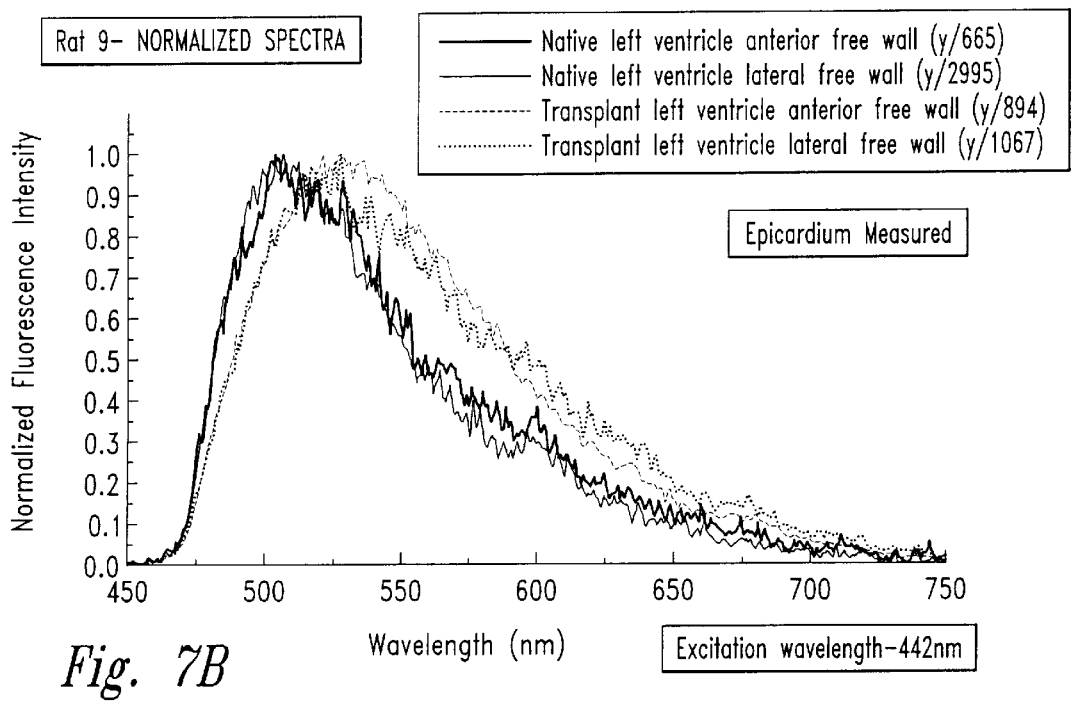
Figure 20:
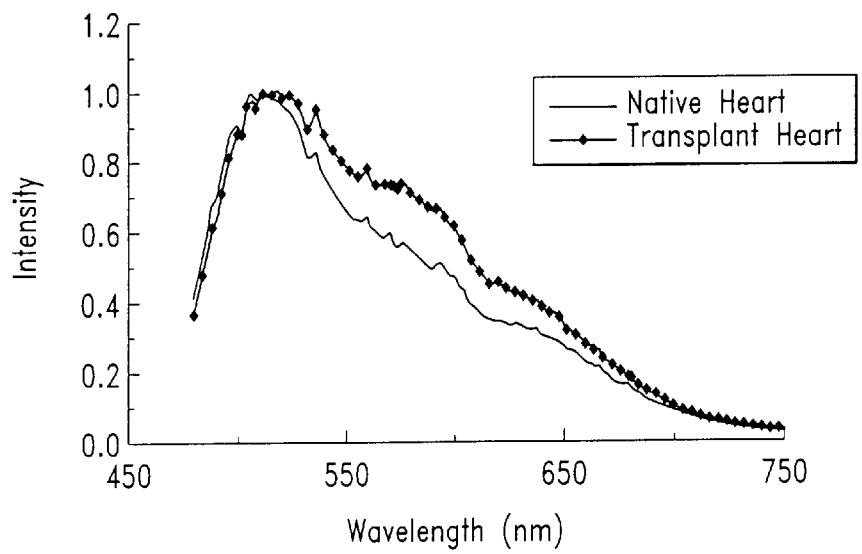
FIGS. 20–22 depict graphs that depict waveform contour analysis correlated to severity of rejection.
Figure 21:
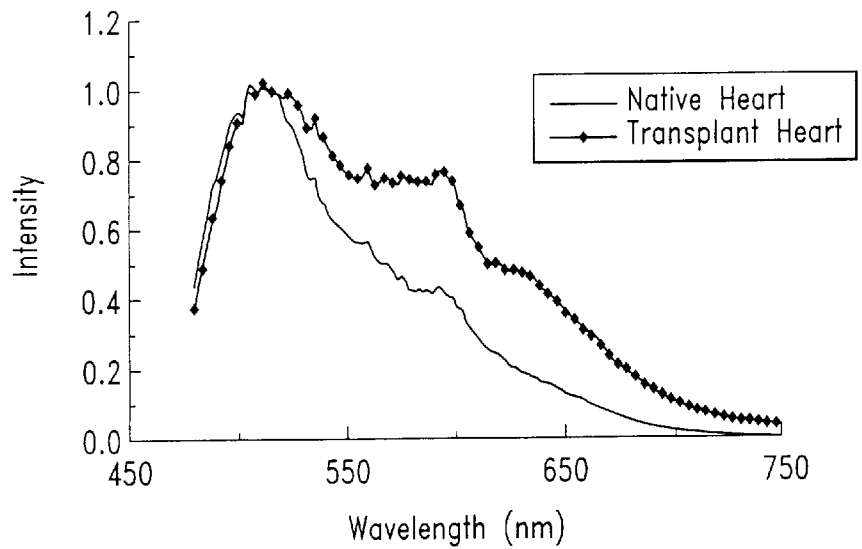
Figure 22:
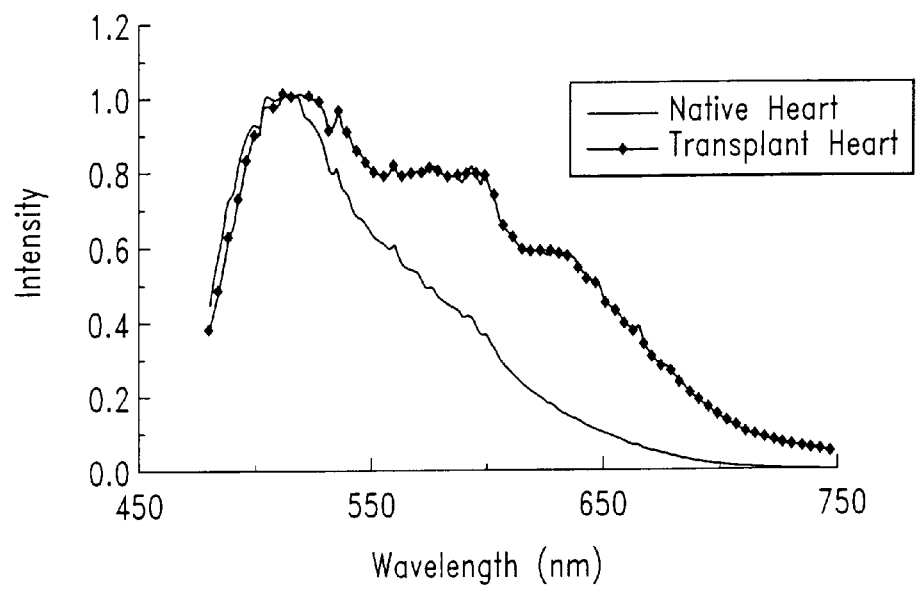

C. Results:

Ten rat abdominal cardiac allografts underwent 201 spectral measurements. Fluorescence spectra from normal cardiac tissue and transplanted tissue at 442 nm excitation wavelengths were shown in FIGS. 5a through 7b. Normal tissue consistently had a narrower spectral peak with consistently dampened fluorescence intensity (au) as compared to transplanted tissue. The latter tissue thus had significantly broader and higher level fluorescence intensity, whether sampled optically in the endocardium (FIGS. 5a and 5b), in the myocardium (FIGS. 6a and 6b), or on the epicardium (FIGS. 7a and 7b). The waveform contour was consistently broader in the transplanted hearts and had a spectral peak shifted to longer wavelenths. In FIG. 8, the difference in fluorescent qualities of normal and allograft myocardium was represented in color images of fluorescence at different red/green image gain ratios. The image gain ratio was the ratio of the intensity amplification of the red image versus the intensity amplification of the green image where the red image was the image in the wavelength range 630 nm and above, and the green image is the image in the wavelength range of 490 nm to 560 nm. In addition to the fact that the normal heart tissue was consistently green regardless of the gain ratio, certain hearts with moderate injury required a higher gain ratio in order for the image to be more predominantly orange-red, while more severely injured myocardium (images g, h, and i in FIG. 8) becomes yellow-orange-red at a lower red-green image gain ratio. Thus, not only the presence of rejection may be detected, but also the severity of rejection can be discerned. Waveform contour analysis of other samples also showed that the severity of rejection can be discerned. See FIGS. 20–22.

Example 2

Optical Biopsy In Vivo Of A Human Being

After determining that the patient is not excluded from the procedure, perform a standard diagnostic cardiac catheterization procedure in order to introduce an optical bioptome into the heart. Such procedure can comprise a standard right heart catheterization performed percutaneously from the right internal jugular vein as described below. A 9 F sheath is used initially, which can accommodate a standard 7 F end-hold catheter or 7 F balloon-directed floating thermodilution catheter.

A cap is placed over the patient's hair and a pillow is positioned under the shoulders and neck in order to slightly hyperextend the neck. Care is taken to position the head in line with the long axis of the body, with the patient facing to the left. The right side of the neck is prepped and draped using standard sterile technique. Gentle pressure is then placed on the patient's mandible, and the patient is asked to raise his head slightly off the pillow (no more than 2 in.). This causes the sternomastoid muscle to contract, thus making it easier to identify landmarks and to mark the position to introduce the sheath. A point on the lateral border of the median head of the sternomastoid muscle at least 6 cm above the clavicle is marked. The area is infiltrated with 2% xylocaine using a 25-gauge needle. A 22-gauge, 1½-in. needle is then attached to the syringe and xylocaine is infiltrated deeply. Care is taken not to enter the carotid artery. The needle is angled caudal and slightly lateral in an attempt to locate the right internal jugular vein, which lies directly under the lateral head of the sternocleidomastoid muscle. After the area is adequately anesthetized a small stab wound is made in the skin with a #11 scalpel blade and the subcutaneous tissue is spread apart with a small straight clamp. A 10-cc syringe containing a small amount of saline is attached to a 22-gauge needle. The patient is instructed to perform the Valsalva maneuver, in order to increase venous pressure. It is also helpful to raise the patient's legs, thus further increasing venous pressure. The needle is then advanced slowly, angling the tip both caudal and slightly lateral so that it penetrates just under the lateral head of the sternomastoid muscle. Constant suction is maintained on the syringe in order to identify when the needle first enters the internal jugular vein. The needle is not advanced through the back wall of the vein, thus minimizing the possibility of bleeding into the carotid sheath. The syringe is detached and the needle left in place in order to act as a guide. An 18-gauge Amplatz® or Cournand needle is attached to the syringe. Using constant suction, the needle is advanced slowly following the course of the 22-gauge needle. When the internal jugular vein is entered, a short straight guide wire is passed through the 18-gauge needle, the needle removed, and the false catheter-dilator and sheath are then positioned in the internal jugular vein using standard technique. The side-arm of the sheath is fitted with a stopcock to prevent an air embolus. The side-arm and sheath are then flushed with heparanized saline.

The optical bioptome is prepared by curving it at a 45° angle approximately 7 cm from the tip. The bend is in alignment with the optical bioptome handle, thus facilitating proper manipulation of the tip in the heart. The patient is asked to suspend breathing and the optical bioptome is advanced quickly into the sheath, pointing the tip towards the lateral border of the heart (the patient's right side). Fluoroscopy can be used at this point in order to ensure that the optical bioptome does not inadvertently enter the right subclavian vein. When the optical bioptome is in the mid to lower third of the right atrium, the handle is rotated counterclockwise (anterior) to point the tip medially. The tip of the optical bioptome is then advanced across the tricuspid valve. Occasional difficulty in crossing the tricuspid valve will be encountered. A slightly different bend on the optical bioptome or rotating the optical bioptome at a different level in the right atrium will facilitate crossing the tricuspid valve. After crossing into the right ventricle the optical bioptome handle is rotated further counterclockwise so that it is now pointing posteriorly; the optical bioptome tip should also be pointed in this direction. The posterior position of the optical bioptome tip can be verified using a C-arm type fluoroscope is available. The tip is then advanced until it meets resistance (at this point the operator should feel the cardiac impulse) or until ventricular premature depolarizations are induced. The tip is now in the area of the right ventricular apex pointing towards the ventricular septum. On fluoroscopy the tip should be at the level or slightly caudal to the top of the left diaphragm.

An optical biopsy of the tissue is obtained by administering excitation light at a wavelength of 442 nm in accordance with the procedure outlined above in Example 1B. The resulting fluorescence is analyzed to determine if the tissue provides a significantly broader and higher level fluorescence intensity, and/or is significantly red-shifted when compared with healthy tissue of the same type, similar to the analysis described above in Example 1C.

In the event that the optical biopsy suggests that tissue biopsy is indicated, the optical bioptome is withdrawn 1 to 2 cm and the jaws opened. This tends to straighten the bend in the optical bioptome, pointing the tip more towards the apex of the right ventricle. Such straightening of the optical bioptome can also be effected prior to obtaining the optical biopsy, if desired (typically such early straightening is effected without opening the jaws of the bioptome). The optical bioptome is again advanced until resistance is felt or ventricular premature depolarizations are induced. The jaws of the optical bioptome are then closed. Occasionally, it is necessary to pause approximately 2 to 5 sec to allow the jaws to close completely. The bioptome is then withdrawn rapidly and in the same motion rotated clockwise (anteriorly) back to the right atrium. Initially, significant resistance will be experienced, but then there will be a sudden release of tension and the bioptome can be quickly withdrawn from the right ventricle. The patient is then asked to suspend breathing and the bioptome is withdrawn from the sheath. The jaws of the bioptome are opened and the size of the sample is examined. The sample is removed using fine forceps. Care is taken not to crush the sample. It is then placed in room temperature fixative for later study.

When manipulating the bioptome into the right ventricle, it is preferred that the bioptome is rotated anteriorly, thus avoiding accidental entry into the coronary sinus. The biopsy will typically be taken from the ventricular septum in order to avoid the thin free wall of the right ventricle. It is also preferred to remove the biopsy from the apex of the right ventricle in order to avoid the conducting system.

If indicated from the optical biopsy, from three to five tissue biopsy specimens are obtained, each measuring approximately 1 to 2 mm$^3$. Samples are assayed for light and electron microscopy and one specimen frozen for possible subsequent study. Specimens may also be obtained for viral culture or other specialized procedures.

At the conclusion of the procedure the thorax is fluoroscoped to look for evidence of either pericardial effusion, pleural effusion, or pneumothorax. If any complication is suspected a standard chest film or echocardiogram may be obtained. The patient is then put in a sitting position to lower venous pressure, asked to suspend breathing, and the sheath is removed. Pressure is applied to the area above and below the puncture site for at least 10 min. The puncture site is then covered with a Band-Aid ®-type bandage.

Example 3

This evaluation employs the abdominal allograft model (Lewis to F344) which allows for the heart from the rat receiving the transplant to serve as an internal control. Lewis-Lewis isografts are also planned as controls. Allografts (different rat strains) and isografts (same rat strains) will be treated with cyclosporin or left untreated.

The donor and recipient rats are prepared and then sacrificed, as outlined above in Example 1.

For each rat, sections from the native heart, the spleen and the transplant heart are cut onto a single slide. Sections cut at 5 μm are stained with Hemotoxylin & Eosin (H&E), Masson's trichrome and Movat's pentachrome. The slides stained with H&E are evaluated by a pathologist and scored using the ISHLT grading system as well as other pathologic indices.

FIGS. 24a–24e depict a graph of several spectra that differ according to the level of rejection experienced by the target tissue, along with photographs of corresponding tissue sections. FIGS. 24a–24e help illustrate changes in the autofluorescence spectra after the onset of tissue rejection: a shifting of the main peak to longer wavelengths and an increase in spectral weight in the 520 nm–600 nm region. Another salient feature of the graph in FIG. 24a is a distinct sub-peak in the control spectrum at 600 nm that largely disappears in spectra from tissue exhibiting rejection.

Figure 25A:
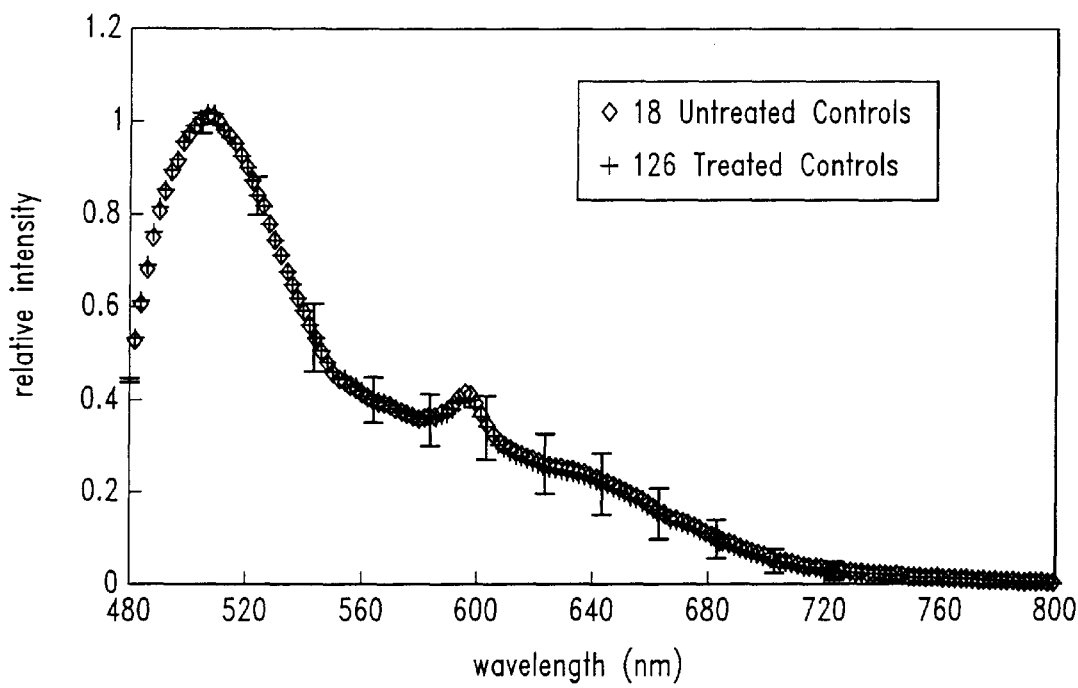
FIG. 25a is a graph depicting averaged spectra of hearts from control rats that had not been treated with cyclosporin compared to averaged spectra of hearts from rats treated with cyclosporin.
Figure 25B:
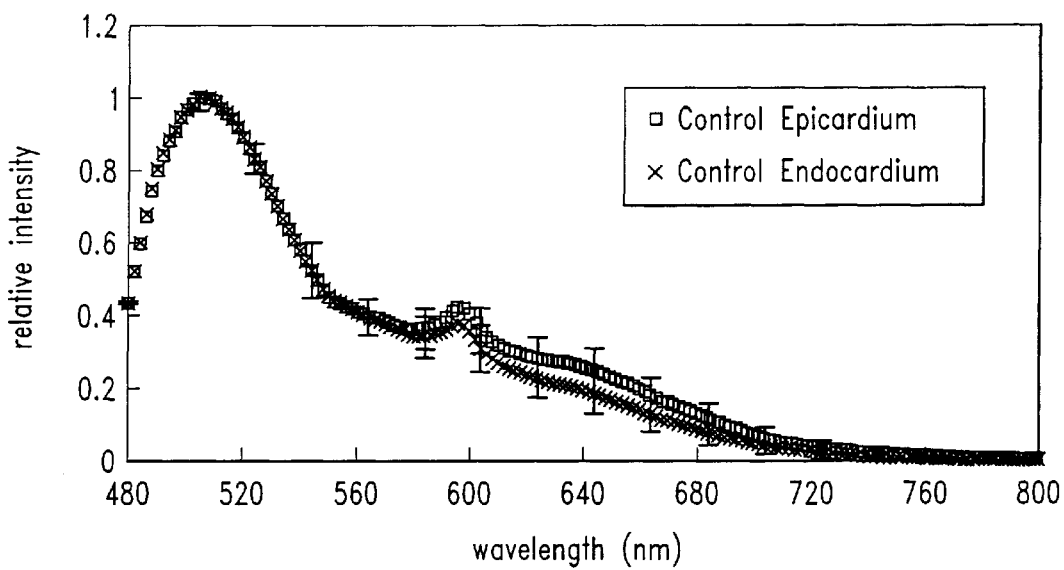
FIG. 25b is a graph depicting averaged spectra showing intrinsic differences between the autofluorescence of epicardium and endocardium.

Immunosuppression therapy with cyclosporin was used on a large subset of the rats described above because of its key role in the management of heart rejection in human patients. It was intended to determine whether it had unforeseen effects regarding tissue autofluorescence that might obscure real changes associated with inflammation due to rejection. FIG. 25a compares the average autofluorescence spectrum of 118 non-transplant control spectra taken from hearts that had not been treated with cyclosporin and 126 similar spectra taken from hearts that had been treated with cyclosporin. There is excellent agreement between the two average spectra, indicating that cyclosporin in and of itself is not contributing to any anomalous fluorescence that might be masked as intrinsic tissue autofluorescence. FIG. 25b depicts the same non-transplant control dataset as in FIG. 25a but this time divided into averaged spectra corresponding to epicardium and endocardium. There is an intrinsic difference between endocardium and epicardium: a greater ratio of green wavelengths (near the main peak at ~520 nm) to longer wavelengths is formed in the epicardium. This is consistent with the appearance of the epicardium, which is brighter green than the endocardium, when viewed under a fluorescence microscope.

To quantify the variations in the autofluorescence spectra as the tissue rejection progresses, a linear discriminant function analysis (DFA) with a stepwise feature selection of single wavelength values was used. Care should be taken, however, that there are no spectra in the dataset used for the stepwise selection procedures that have clearly identifiable spectral features that are not necessarily correlated with the tissue rejection/inflammatory response process. A primary example is that of absorption of light by hemoglobin: the absorption coefficient of red blood cells changes by more than an order of magnitude within the visible range (480 nm–800 nm). Hemoglobin has a characteristic "double-bumped" absorption spectrum having maxima at 540 nm and 580 nm. This can be used as a signature facilitating visual and/or linear function discrimination. It was quite common to find a pair of minima in the autofluorescence spectra corresponding to hemoglobin absorption. The tissue rejection process can involve hemorrhaging and the heterotopic transplant heart tends to be prone to thrombi. Such can have so many red blood cells present that the main peak of the signal is near 640 nm with shorter wavelengths being heavily suppressed. Before proceeding with an analysis of the spectra in terms of their ISHLT grade, spectra displaying blood absorption characteristics were removed from consideration: first, a subset of these spectra was identified by visual inspection and then this subset was used as one group in a stepwise feature selection, the other group being all the remaining spectra; the linear discriminant function thus identified was then used to score all the spectra which isolated the majority of the blood absorption-contaminated spectra in a single group.

Figure 26A:
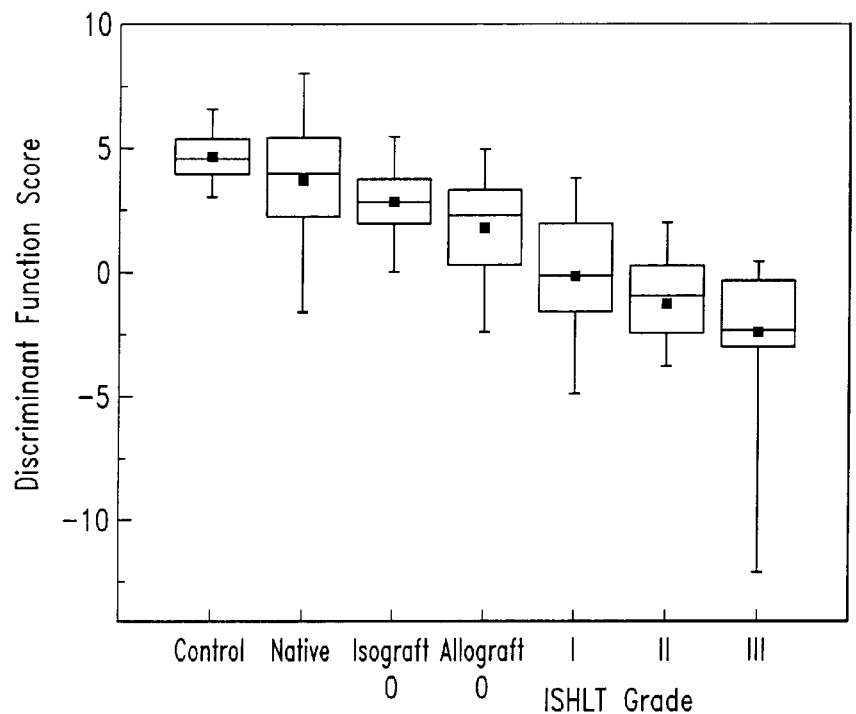
FIG. 26a depicts a stepwise feature selection based on grade 0 and grade III rejection based on endocardium and epicardium.

The remaining spectra were found to be free of the blood absorption effects and could be analyzed with further discriminant functions. Initially, all endocardium and epicardium spectra were group into one data set and then separated into an ISHLT grade 0 group and an ISHLT grade III group. DFA was performed and a five-feature DF generated. The wavelength values used were 480, 496, 504, 518 and 522 nm. These wavelengths were in the area of the position and shape changes of the main peak visually observed in the autofluorescence spectra. This DF was then used to score spectra from all grades including spectra from native hearts and control hearts. The results are shown in the box-plot in FIG. 26a. A clear progression of decreasing DF scores with increasing tissue rejection severity is evident with high statistical differences (2-population T-test, p<0.005) between the ISHLT grade 0, grade I and grade II groups. The ISHLT grade II and III groups were statistically different at the p=0.05 level. The data was not divided beforehand into a training and test set; the DF was trained only on the ISHLT grade I and grade III groups. Thus the controls, natives, grade I and grade II groups are fair tests of the DF performance.

Figure 26B:
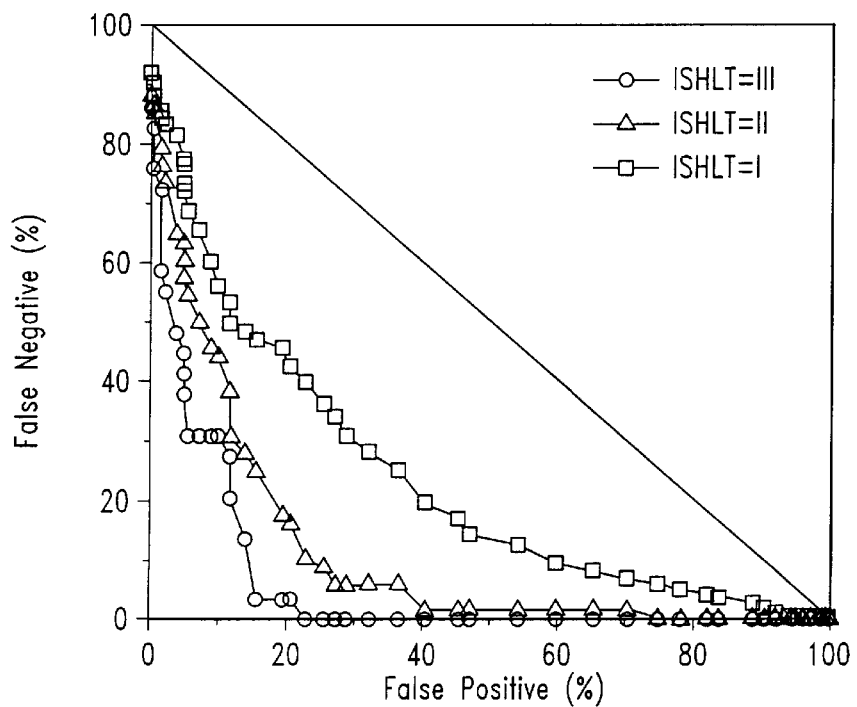
FIG. 26b is a graft ROC plot treating ISHLT grade 0 as a "normal" group.

FIG. 26b is a Receiver Operator Characteristic (ROC) plot for a test of grades I, II and III versus grade 0 (which was designated the "normal" group for this purpose). The III vs. 0 test had the best performance although even the I vs. 0 gives a 30% False Positive/30% False Negative rate for a DF score threshold of ~2.0. Other discriminant functions can be generated in view of the present disclosure that are more specific to grades 0/I discrimination and give better performance.

Figure 27A:
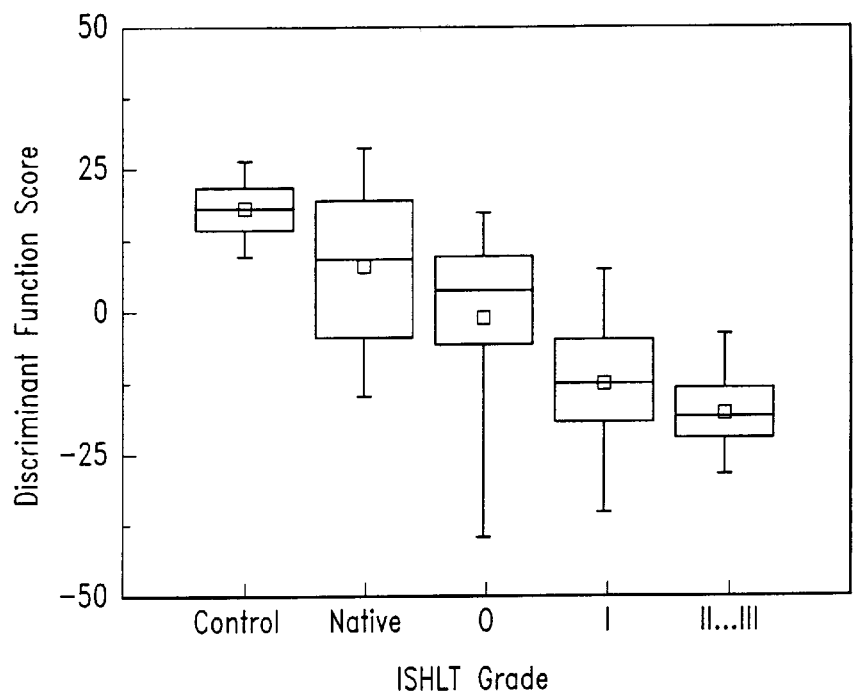
FIG. 27a comprises a box plot of discriminant function scores for endocardium and epicardium wherein the discriminant function scores were trained on control versus grades II & III.

FIG. 27a shows the performance of a discriminant function that uses the control group and a group consisting of grades I and III as the training set. Combining grades II and III into one group gives a larger training set, which helps to give a more robust discriminant function. Using a small training set runs the risk of over-fitting the data, i.e., the discriminant function performs well on the training set but poorly on other data sets. In this case, the grade 0 group was included along with the native and grade I group in the test set. The discriminant function separated the groups.

Figure 27B:
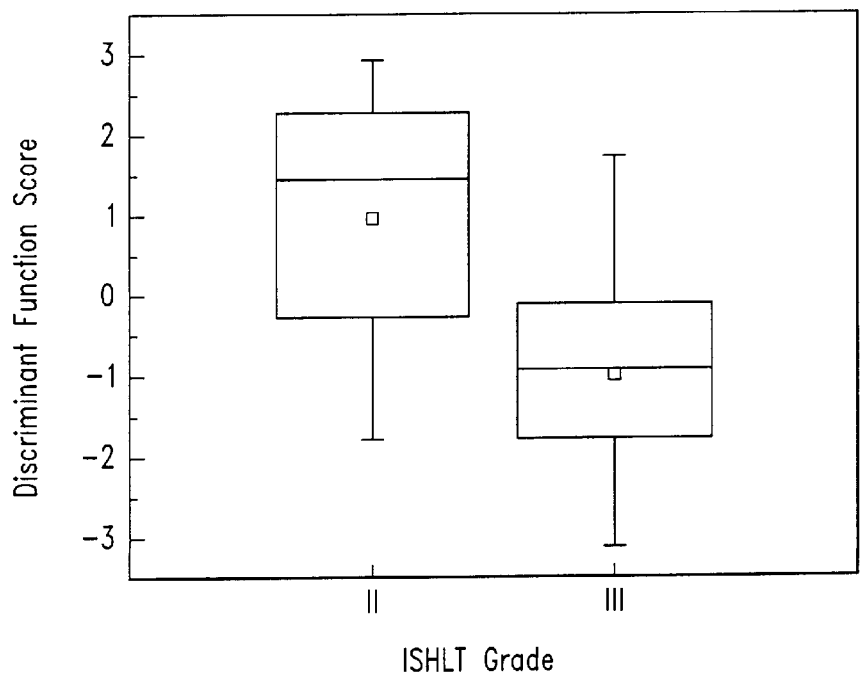
FIG. 27b depicts a box plot of discriminant function scores for endocardium and epicardium trained on grade II versus grade III.

FIG. 27b is the box-plot of the DF scores of the grade II versus grade III group where the DF was trained on these two groups. A good separation in DF scores and a highly statistically significant difference between the two groups results although it must be noted that the training and the test sets are the same.

Figure 28A:
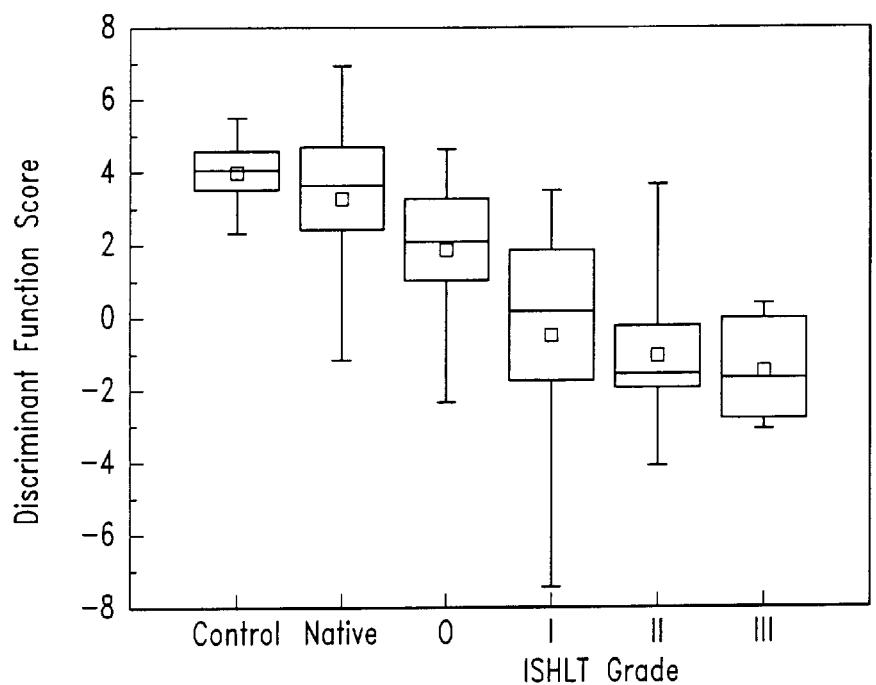
FIG. 28a depicts epicardium discriminant function scores wherein the discriminant function was trained on grade 0 versus grade III from endocardium.
Figure 28B:
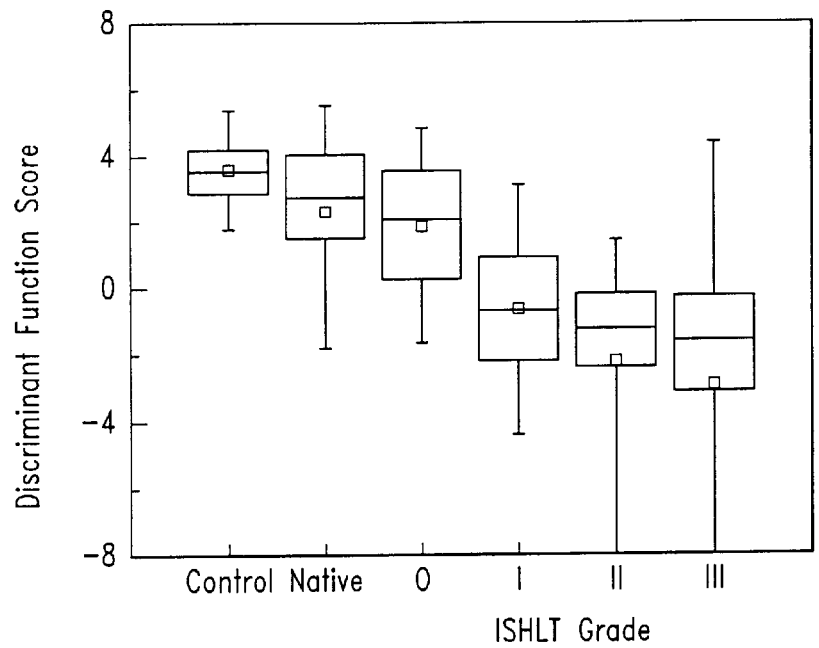
FIG. 28b depicts endocardium discriminant function scores wherein the discriminant function was trained on grade 0 versus grade III from epicardium.

FIGS. 28a and 28b illustrate a more severe test of the discrimination between the spectra from the different ISHLT grades. Here, the spectra were divided into epicardium and endocardium groups prior to any DFA. The discriminant function in FIG. 28a was trained on endocardium spectra from grades 0 and III and the resulting box-plot of the DF scores for the epicardium spectra is shown in the figure—all groups shown are independent tests of the DF performance. There is still a monotonic decrease in mean DF scores for groups of increasing rejection severity and highly statistically significant differences (p<0.005) between grades 0 and any of grades I, II and III. However, the discrimination between intermediate stages of rejection is not as good as in FIG. 26a. This decrease in performance is most likely due to the smaller amount of data used as the training set as discussed above. Another manifestation of this is the greater intra-group variability of the DF scores, which blurs inter-group differences. FIG. 28b is analogous to FIG. 28a except that the DF training was done on the epicardium spectra and the results shown are for the scored endocardium spectra. This box-plot is qualitatively similar to FIG. 28a and the same conclusions apply. The training set for this DF is even smaller than for FIG. 28a, and this is reflected by the even larger spread in DF scores within the groups. These are in spite of the intrinsic differences between epicardium and endocardium autofluorescence spectra discussed above.

Although the present invention had been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

We claim:

1. A method for determining whether a transplanted tissue comprises one or more characteristics indicative of rejection by a host, the method comprising:

a) illuminating the transplanted tissue under conditions suitable to cause the transplanted tissue to fluoresce;

b) collecting the fluorescence to provide a transplant fluorescence signature; and c) comparing the transplant fluorescence signature with a known fluorescence signature representative of a same type of tissue as the transplanted tissue, and therefrom determining whether the transplanted tissue exhibits one or more characteristics indicative of rejection, wherein the method is implemented using a catheter or endoscope that comprises at least one illumination light guide that conducts light to the transplanted tissue to illuminate the transplanted tissue and at least one collection light guide that collects fluorescence from the transplanted tissue, and wherein the method further comprises collecting a plurality of transplant fluorescence signatures, wherein at least two of the plurality of transplant fluorescence signatures comprise a significant fluorescence contribution from a plurality of selected different depths of the transplanted tissue to provide at least two different fluorescence signatures.

2. The method of claim 1 wherein the catheter or endoscope comprises at least a first collection light guide and a second collection light guide each of which is spaced a different distance from its associated illumination light guide, and wherein the collection of the at least two different fluorescence signatures comprises collecting light using each of the first collection light guide and the second collection guide during the collecting steps.

3. The method of claim 2 wherein the illumination light guide associated with the first collection light guide and the second collection light guide is a single light guide.

4. The method of claim 1 wherein the step of comparing comprises comparing the wavelength of maximum intensity of the transplant fluorescence signature with the healthy fluorescence signature.

5. A method for determining whether a transplanted tissue comprises one or more characteristics indicative of rejection by a host, the method comprising:

a) illuminating the transplanted tissue under conditions suitable to cause the transplanted tissue to fluoresce;

b) collecting the fluorescence to provide a transplant fluorescence signature; and c) comparing the transplant fluorescence signature with a known fluorescence signature representative of the same type of tissue as the transplanted tissue, and therefrom determining whether the transplanted tissue exhibits one or more characteristics indicative of rejection, wherein the transplanted tissue is illuminated with light that does not comprise UV light.

6. A method for determining whether a transplanted tissue comprises one or more characteristics indicative of rejection by a host, the method comprising:

a) illuminating the transplanted tissue under conditions suitable to cause the transplanted tissue to fluoresce;

b) collecting the fluorescence to provide a transplant fluorescence signature; and c) comparing the transplant fluorescence signature with a known fluorescence signature representative of the same type of tissue as the transplanted tissue, and therefrom determining whether the transplanted tissue exhibits one or more characteristics indicative of rejection, wherein the transplanted tissue is illuminated with light that consists essentially of blue light.

7. A method for determining whether a transplanted tissue comprises one or more characteristics indicative of rejection by a host, the method comprising:

a) illuminating the transplanted tissue under conditions suitable to cause the transplanted tissue to fluoresce;

b) collecting the fluorescence to provide a transplant fluorescence signature; and c) comparing the transplant fluorescence signature with a known fluorescence signature representative of the same type of tissue as the transplanted tissue, and therefrom determining whether the transplanted tissue exhibits one or more characteristics indicative of rejection, wherein the transplanted tissue is illuminated with light that consists essentially of a wavelength of about 442 nm.

8. A method for determining whether a transplanted tissue comprises one or more characteristics indicative of rejection by a host, the method comprising:

a) illuminating the transplanted tissue under conditions suitable to cause the transplanted tissue to fluoresce;

b) collecting the fluorescence to provide a transplant fluorescence signature; and c) comparing the transplant fluorescence signature with a known fluorescence signature representative of the same type of tissue as the transplanted tissue, and therefrom determining whether the transplanted tissue exhibits one or more characteristics indicative of rejection, wherein the step of illuminating comprises illuminating light from an illumination light guide, and the step of collecting comprises collecting the fluorescence in a collection light guide.

9. A method for determining whether a transplanted tissue comprises one or more characteristics indicative of rejection by a host, the method comprising:

a) illuminating the transplanted tissue under conditions suitable to cause the transplanted tissue to fluoresce;

b) collecting the fluorescence to provide a transplant fluorescence signature; and c) comparing the transplant fluorescence signature with a known fluorescence signature representative of the same type of tissue as the transplanted tissue, and therefrom determining whether the transplanted tissue exhibits one or more characteristics indicative of rejection, wherein the steps of illuminating and collecting are performed in vivo during a single diastole of a heartbeat of the host.

10. The method of claim 9 wherein the steps of illuminating and collecting during a single diastole are initiated using one or more signals of an electrocardiogram.

11. The method of claim 9 wherein the steps of illuminating and collecting during a single diastole are initiated using a blood pressure pulse of the host.

12. The method of claim 11 wherein the blood pressure pulse is measured using a blood pressure monitor located externally to the host.

13. The method of claim 12 wherein the wavelength bands are measured by broad band optical detectors.

14. The method of claim 11 wherein the blood pressure pulse is measured by a pulse oximeter.

15. The method of claim 14 wherein the method further comprises selecting a specific spectral region using an optical band pass filter.

16. A method for determining whether a transplanted tissue comprises one or more characteristics indicative of rejection by a host, the method comprising:
 a) illuminating the transplanted tissue under conditions suitable to cause the transplanted tissue to fluoresce;
 b) collecting the fluorescence to provide a transplant fluorescence signature; and
 c) comparing the transplant fluorescence signature with a known fluorescence signature representative of the same type of tissue as the transplanted tissue, and therefrom determining whether the transplanted tissue exhibits one or more characteristics indicative of rejection,
 wherein the step of comparing comprises comparing a full width at half maximum (FWHM) of the transplant fluorescence signature with the healthy fluorescence signature.

17. A method for determining whether a transplanted tissue comprises one or more characteristics indicative of rejection by a host, the method comprising:
 a) illuminating the transplanted tissue under conditions suitable to cause the transplanted tissue to fluoresce;
 b) collecting the fluorescence to provide a transplant fluorescence signature; and
 c) comparing the transplant fluorescence signature with a known fluorescence signature representative of the same type of tissue as the transplanted tissue, and therefrom determining whether the transplanted tissue exhibits one or more characteristics indicative of rejection,
 wherein the step of comparing comprises comparing a ratio of the integrated intensity of two or more wavelength bands of the transplant fluorescence signature with the healthy fluorescence signature.

18. The method of any one of claims 1 to 8 or 16 to 4 wherein the transplanted tissue is illuminated and the fluorescence is collected in vivo.

19. The method of any one of claims 1–4 wherein the host is a human.

20. The method of any one of claims 1–4 wherein at least one step of the method is computer implemented.

* * * * *